US012758490B2

(12) United States Patent
Goldstein et al.

(10) Patent No.: US 12,758,490 B2
(45) Date of Patent: Oct. 13, 2026

(54) HYDROGEL IMPLANTS FOR LOWERING INTRAOCULAR PRESSURE

(71) Applicant: OCULAR THERAPEUTIX, INC., Bedford, MA (US)

(72) Inventors: Michael Goldstein, Cambridge, MA (US); Arthur Driscoll, Reading, MA (US); Charles D. Blizzard, Nashua, NH (US); Ankita Desai, Reading, MA (US)

(73) Assignee: Ocular Therapeutix, Inc., Bedford, MA (US)

( * ) Notice: Subject to any disclaimer, the term of this patent is extended or adjusted under 35 U.S.C. 154(b) by 219 days.

(21) Appl. No.: 18/384,564

(22) Filed: Oct. 27, 2023

(65) Prior Publication Data

US 2024/0165018 A1 May 23, 2024

Related U.S. Application Data

(63) Continuation of application No. 16/857,464, filed on Apr. 24, 2020, now abandoned.

(60) Provisional application No. 62/970,828, filed on Feb. 6, 2020, provisional application No. 62/840,134, filed on Apr. 29, 2019, provisional application No. 62/838,791, filed on Apr. 25, 2019.

(51) Int. Cl.

| | |
|---|---|
| ***A61K 9/00*** | (2006.01) |
| ***A61K 31/215*** | (2006.01) |
| ***A61P 27/02*** | (2006.01) |
| ***A61P 27/06*** | (2006.01) |

(52) U.S. Cl.

CPC .......... *A61K 9/0024* (2013.01); *A61K 9/0051* (2013.01); *A61K 31/215* (2013.01); *A61P 27/02* (2018.01); *A61P 27/06* (2018.01)

(58) Field of Classification Search

CPC .. A61K 9/0024; A61K 9/0051; A61K 31/215; A61P 27/02; A61P 27/06

See application file for complete search history.

(56) References Cited

U.S. PATENT DOCUMENTS

| | | | |
|---|---|---|---|
| 3,949,750 | A | 4/1976 | Freeman |
| 3,993,071 | A | 11/1976 | Higuchi |
| 4,915,684 | A | 4/1990 | MacKeen |
| 5,469,867 | A | 11/1995 | Schmitt |
| 5,902,598 | A | 5/1999 | Chen |
| 6,027,470 | A | 2/2000 | Mendius |
| 6,196,993 | B1 | 3/2001 | Cohan |
| 6,437,152 | B1 | 8/2002 | Jackson |
| 6,509,327 | B1 | 1/2003 | Cagle |
| 6,646,001 | B2 | 11/2003 | Hellberg |
| 6,982,090 | B2 | 1/2006 | Gillespie |
| 7,109,371 | B2 | 9/2006 | Clissold |
| 7,166,730 | B2 | 1/2007 | Gutman |
| 7,897,795 | B2 | 3/2011 | Henschke |
| 7,998,497 | B2 | 8/2011 | de Juan, Jr. |
| 8,178,582 | B2 | 5/2012 | Kabra |
| 8,268,299 | B2 | 9/2012 | Kabra |
| 8,323,630 | B2 | 12/2012 | Kabra |
| 8,388,941 | B2 | 3/2013 | Chowhan |
| 8,409,606 | B2 | 4/2013 | Sawhney |
| 8,436,194 | B2 | 5/2013 | Henschke |
| 8,476,471 | B2 | 7/2013 | Yiannikouros |
| 8,512,738 | B2 | 8/2013 | Edelman |
| 8,512,749 | B2 | 8/2013 | Sawhney |
| 8,519,178 | B2 | 8/2013 | Hogan |
| 8,535,705 | B2 | 9/2013 | Pathak |
| 8,563,027 | B2 | 10/2013 | Jarrett |
| 8,685,435 | B2 | 4/2014 | Nivaggioli |
| 8,691,265 | B2 | 4/2014 | de Juan, Jr. |
| 8,715,712 | B2 | 5/2014 | de Juan, Jr. |
| 8,742,143 | B2 | 6/2014 | Henschke |
| 8,747,884 | B2 | 6/2014 | de Juan, Jr. |
| 8,754,123 | B2 | 6/2014 | Kabra |
| 8,846,073 | B2 | 9/2014 | Spada |
| 8,900,662 | B2 | 12/2014 | Lee |
| 8,901,319 | B2 | 12/2014 | Chambournier |
| 8,956,655 | B2 | 2/2015 | Lyons |
| 8,957,240 | B2 | 2/2015 | Hogan |
| 8,961,501 | B2 | 2/2015 | Jarrett |
| 9,061,065 | B2 | 6/2015 | Robinson |
| 9,115,109 | B2 | 8/2015 | Wei |
| 9,125,807 | B2 | 9/2015 | Sawhney |
| 9,126,898 | B2 | 9/2015 | Oh |
| 9,144,561 | B2 | 9/2015 | Kabra |
| 9,149,428 | B2 | 10/2015 | Spada |
| 9,168,222 | B2 | 10/2015 | de Juan, Jr. |
| 9,187,593 | B2 | 11/2015 | Dadey |
| 9,205,150 | B2 | 12/2015 | Jarrett |

(Continued)

FOREIGN PATENT DOCUMENTS

| | | | |
|---|---|---|---|
| WO | 2009008946 | A1 | 1/2009 |
| WO | 2010093873 | A2 | 8/2010 |

(Continued)

OTHER PUBLICATIONS

Bacharach et al., "Phase 3, Randomized, 20-Month Study of the Efficacy and Safety of Bimatoprost Implant in patients with Open-Angle Glaucoma and Ocular Hypertension (ARTEMIS 2)"_ Drugs, vol. 81 No. 17, pp. 2017-2033, published by Adis.

Blizzard, et al., "Efficacy and Pharmacokinetics of a Sustained Release Travoprost Intracameral Hydrogel Implant in Beagle Dogs," presented at the Association for Research in Vision and Ophthalmology 2018 Annual Meeting: Honolulu, HI, Apr. 29-May 3, 2018, 1 pg.

Blizzard, et al., "Pharmacokinetics of OTX-TIC, a Sustained Release Travoprost Intracameral Implant in Rabbits," Presented at the Assciation for Research in Vision and Ophthalmology Annual Meeting: Vancover, Canada, Apr. 28-May 2, 2019, 1 pg.

Blizzard, et al.,, Preclinical Assessment of OTX-TIC (Travoprost) Biodegradable Hydrogel Intracameral Implant for the Treatment of Glaucoma, ASCRS 2018, Apr. 15, 2018, 8 pgs.

(Continued)

*Primary Examiner* — Zohreh A Fay

(74) *Attorney, Agent, or Firm* — Lowenstein Sandler LLP

(57) ABSTRACT

Provided herein are sustained release biodegradable ocular hydrogel implants which are useful for lowering ocular pressure and for treating related conditions.

15 Claims, 16 Drawing Sheets

(56) References Cited

U.S. PATENT DOCUMENTS

| | | | |
|---|---|---|---|
| 9,212,125 | B2 | 12/2015 | Kardos |
| 9,254,267 | B2 | 2/2016 | Sawhney |
| 9,278,139 | B2 | 3/2016 | Rau |
| 9,290,432 | B2 | 3/2016 | Bischof |
| 9,370,485 | B2 | 6/2016 | Sawhney |
| 9,393,223 | B2 | 7/2016 | Hughes |
| 9,421,126 | B2 | 8/2016 | Alster |
| 9,445,944 | B2 | 9/2016 | Rapacki |
| 9,463,114 | B2 | 10/2016 | Odrich |
| 9,464,028 | B2 | 10/2016 | Wei |
| 9,492,316 | B2 | 11/2016 | Ghebremeskel |
| 9,504,653 | B2 | 11/2016 | Liu |
| 9,504,696 | B2 | 11/2016 | Robinson |
| 9,540,311 | B2 | 1/2017 | Wei |
| 9,549,852 | B2 | 1/2017 | de Juan, Jr. |
| 9,555,045 | B2 | 1/2017 | Garrigue |
| 9,561,282 | B2 | 2/2017 | Dadey |
| 9,572,800 | B2 | 2/2017 | Zarnitsyn |
| 9,636,189 | B2 | 5/2017 | Ahari |
| 9,707,173 | B2 | 7/2017 | Kabra |
| 9,707,238 | B2 | 7/2017 | Chang |
| 9,750,636 | B2 | 9/2017 | Rubin |
| 9,775,906 | B2 | 10/2017 | Sawhney |
| 9,828,356 | B2 | 11/2017 | Wei |
| 9,849,082 | B2 | 12/2017 | de Juan, Jr. |
| 9,931,330 | B2 | 4/2018 | Zarnitsyn |
| 9,937,073 | B2 | 4/2018 | de Juan, Jr. |
| 9,949,942 | B2 | 4/2018 | Butuner |
| 10,004,636 | B2 | 6/2018 | Alster |
| 10,010,610 | B2 | 7/2018 | Horn |
| 10,064,872 | B2 | 9/2018 | Chang |
| 10,100,028 | B2 | 10/2018 | Yiannikouros |
| 10,111,886 | B2 | 10/2018 | Ng |
| 10,226,417 | B2 | 3/2019 | Jarrett |
| 10,245,178 | B1 | 4/2019 | Heitzmann |
| 10,251,954 | B2 | 4/2019 | Sawhney |
| 10,278,919 | B2 | 5/2019 | Robinson |
| 10,300,014 | B2 | 5/2019 | de Juan, Jr. |
| 10,383,817 | B2 | 8/2019 | de Juan, Jr. |
| 10,420,724 | B2 | 9/2019 | Jarrett |
| 10,434,009 | B2 | 10/2019 | Rapacki |
| 10,441,543 | B2 | 10/2019 | Spada |
| 10,456,293 | B2 | 10/2019 | Rubin |
| 10,617,563 | B2 | 4/2020 | Jarrett |
| 10,671,563 | B2 | 6/2020 | Hack |
| 10,736,774 | B2 | 8/2020 | Alster |
| 10,744,099 | B2 | 8/2020 | Libin |
| 10,786,462 | B2 | 9/2020 | Jarrett |
| 10,835,416 | B2 | 11/2020 | de Juan |
| 10,849,656 | B2 | 12/2020 | Navratil |
| 10,864,218 | B2 | 12/2020 | Hughes |
| 10,874,605 | B2 | 12/2020 | Nivaggioli |
| 10,874,606 | B2 | 12/2020 | de Juan, Jr. |
| 10,905,765 | B2 | 2/2021 | Jarrett |
| 2002/0169409 | A1 | 11/2002 | Gillespie |
| 2003/0108511 | A1 | 6/2003 | Sawhney |
| 2005/0197614 | A1 | 9/2005 | Pritchard |
| 2005/0232972 | A1 | 10/2005 | Odrich |
| 2007/0298075 | A1 | 12/2007 | Borgia |
| 2008/0124400 | A1 | 5/2008 | Liggins |
| 2008/0140192 | A1 | 6/2008 | Humayun |
| 2008/0247984 | A1 | 10/2008 | Messersmith |
| 2010/0278898 | A1 | 11/2010 | Hughes |
| 2012/0059338 | A1 | 3/2012 | Beeley |
| 2012/0156259 | A1 | 6/2012 | Rau |
| 2014/0121612 | A1 | 5/2014 | Rubin |
| 2014/0128478 | A1 | 5/2014 | Asgharian |
| 2014/0371308 | A1 | 12/2014 | Hughes |
| 2015/0272898 | A1 | 10/2015 | Hughes |
| 2015/0374633 | A1 | 12/2015 | Fedorchak |
| 2016/0296627 | A1 | 10/2016 | Garcia |
| 2016/0331738 | A1 | 11/2016 | Jarrett |
| 2016/0354309 | A1 | 12/2016 | Heitzmann |
| 2017/0037002 | A1 | 2/2017 | Vajda |
| 2017/0073323 | A1 | 3/2017 | Wei |
| 2017/0182173 | A1 | 6/2017 | Ng |
| 2018/0085307 | A1 | 3/2018 | Sawhney |
| 2018/0353431 | A1 | 12/2018 | Guo |
| 2019/0021991 | A9 | 1/2019 | Heitzmann |
| 2019/0038636 | A1 | 2/2019 | Vrabec |
| 2019/0216727 | A1 | 7/2019 | Odrich |
| 2019/0224046 | A1 | 7/2019 | Heitzmann |
| 2019/0336441 | A1 | 11/2019 | Whitcup |
| 2020/0038326 | A1 | 2/2020 | Spada |
| 2020/0138701 | A9 | 5/2020 | Odrich |
| 2020/0246222 | A1 | 8/2020 | Malanga |
| 2020/0306182 | A1 | 10/2020 | Das |
| 2020/0337990 | A1 | 10/2020 | Goldstein |
| 2020/0345544 | A1 | 11/2020 | Ketelson |
| 2020/0345750 | A1 | 11/2020 | Chang |
| 2020/0383915 | A1 | 12/2020 | Jablonski |
| 2021/0007973 | A1 | 1/2021 | Patel |
| 2021/0251893 | A1 | 8/2021 | Blizzard |

FOREIGN PATENT DOCUMENTS

| | | | |
|---|---|---|---|
| WO | 2010111449 | A1 | 9/2010 |
| WO | 2013039706 | A1 | 3/2013 |
| WO | 2013086015 | A1 | 6/2013 |
| WO | 2016094646 | A1 | 6/2016 |
| WO | 2016183296 | A1 | 11/2016 |
| WO | 2017015591 | A1 | 1/2017 |
| WO | 2017015616 | A1 | 1/2017 |
| WO | 2017015675 | A1 | 1/2017 |
| WO | 2017019773 | A1 | 2/2017 |
| WO | 2017091749 | A1 | 6/2017 |
| WO | 2018058048 | A1 | 3/2018 |
| WO | 2020219892 | A1 | 10/2020 |

OTHER PUBLICATIONS

Declaration under 37 C.F .R. 1.132 dated Aug. 5, 2021 filed in U.S. Appl. No. 15/714,633, 5 pages.

Driscoll, et al., "Effect of OTX_ TIC, a Sustained Release Travoprost Intracameral Implant on Central Corneal Thickness in Beagles," Presented at the Association for Research in Vision and Ophthalmology Annual Meeting: Vancover, Canada, Apr. 28 May 2, 2019, 1 pg.

Driscoll, et al., "Safety Analysis of a Sustained Release Travoprost Intracameral Hydrogel Implant in Beagle Dogs," Presented at the Association for Research in Vision and Ophthalmology 2018 Annual Meeting: Hanolulu HI, Apr. 29-May 3, 2018, 1 pg.

DURYSTA Prescribing Information, 2020 Allergan, 10 pgs.

Encyclopedia.com "intracameral" [online] retrieved from: https://www.encyclopedia.com/caregiving/dictionarieshesauruses-pictures-and-press-releases/intracameral; on May 26, 2021; 1 page) (Year: 2021).

Error in Measurement {[online] retrieved on Sep. 7, 2021 from: https://mathbitsnotebook.com/Algebra 1 /Units/UN Error.html; 3 pages). (Year: 2021).

Goldstein, et al., "A Prospective Multicenter, Open-Label First-in-Human Study to Evaluate the Safety, Tolerability and Efficacy of OTX-TIC, a Travoprost Intracameral Implant in Subjects with Primary Open-Angel Glaucoma or Ocular Hypertension: Preliminary Findings," Presented at the Association for Research in Vision and Ophthalmology Annual Meeting: Vancover, Canada, Apr. 28 May 2, 2019, 1 pg.

Goldstein, et al., "Evaluating Safety Tolerability and Efficacy of an Intracameral Hydrogel-Based Travoprost Implant in Subjects with Glaucoma or Ocular Hypertension Phase 1 Trail Interim Review," ARVO Annual Meeting, May 2020, 8 pgs.

Goldstein, Michael, "OTX-TIC, an Intracameral Hydrogel-Based Travoprost Implant to Treat Patients with Glaucoma & Ocular Hypertension Phase 1 Trail Update," Glaucoma 360, Jan. 2021, 17 pgs.

Goldstein, Michael, "Transforming Glaucoma Care with Drug Delivery Leveraging a Novel Technology Platform," Glaucoma 360, Feb. 7, 2020, 16 pgs.

Hart, et al., Transforming Glaucoma Care with Drug Delivery Leveraging a Novel Technology Platform, Glaucoma 660, Feb. 1, 2019, 11 pgs.

(56) References Cited

OTHER PUBLICATIONS

International Search Report for PCT/US2020/0029830 mailed Aug. 5, 2020, 4 pages.
International Search Report for PCT/US2021/016889 mailed May 28, 2021, 4 pages.
Langh, et al., "Effect of Hydrogel Persistence on Pharmacodynamics and Tolerability of OTX-TIC, Travoprost Intracameral Implant in Beagles," ARVO Annual Meeting, May 2020, 8 pgs.
Mattessich, et al. "Transforming Drug Delivery Leveraging a Novel Technology Platform," Oct. 10, 2020.
Mattessich, et al., "Transforming Drug Delivery Leveraging a Novel Technology Platform," Sep. 2020.
Ocular Therapeutix™ Reports Second Quarter 2020 Financial Results and Business Update, Newly Published Physician Fee Schedules for 0356T for the Administration of Intracanalicular Inserts to Support Ongoing DEXTENZA® Launch, Firefox, 9 pgs.
Rahic et al., "Novel Drug Delivery Systems Fighting Glaucoma: Formulation Obstacles and Solutions", Pharmaceutics, vol. 13, No. 28, pp. 1-58, published by MDPI.
Walters, et al., "Evaluating Safety, Tolerability and Efficacy of an Intracameral Hydrogel-Based Travoprost Implant in Subjects with Glaucoma Phase 1 Trial Interim Review," ASCRS Annual Meeting, May 16, 2020, 12 pgs.
Walters, et al., Evaluating the Safety, Tolerability and Efficacy of OTX-TIC, a Travoprost Intracameral Implant, in Subjects with Glaucoma: Interim Review, ASCRS 2019, May 5, 2019, 13 pgs.
Written Opinion of the International Searching Authority for PCT/US2020/029830 mailed Aug. 5, 2020, 6 pages.
Written Opinion of the International Searching Authority for PCT/US2021/016889 mailed May 28, 2021, 7 pages.

HYDROGEL IMPLANTS FOR LOWERING INTRAOCULAR PRESSURE

RELATED APPLICATIONS

This application claims priority to U.S. Provisional Application No. 62/838,791, filed Apr. 25, 2019, U.S. Provisional Application No. 62/840,134, filed Apr. 29, 2019, and U.S. Provisional Application No. 62/970,828, filed Feb. 6, 2020, the entire contents of each of which are incorporated herein by reference.

BACKGROUND

Glaucoma is a group of eye disorders that lead to progressive damage to the optic nerve. Glaucoma is the second-leading cause of blindness in the United States and most often occurs in people over age 40. Although there are many theories on the cause of glaucoma, most associate the condition as a result of prolonged increase in the fluid pressure inside the eye. Indeed, lowering intraocular pressure (IOP) is a critical factor for slowing progression for both glaucoma and ocular hypertension. See e.g., Noecker R J, *Ther Clin Risk Manag.* 2006; 2(2): 193-206.

Prostaglandin analogues such travoprost are commonly used as the first line of therapy to effectively lower IOP. However, limitations with the application of topical drops (difficulty with handling the bottle, limited instillation accuracy, potential washout of drops), poor adherence to regimen, and limited bioavailability of topical applications are serious issues affecting IOP control management.

SUMMARY

Provided herein are sustained release ocular hydrogel implants comprising travoprost.

Preclinical studies of the disclosed implants demonstrated acceptable safety profile, maintenance of drug levels in the aqueous humor, and a sustained lowering of intraocular pressure. See Example 1 and 2. In one aspect, e.g., a single dose of the disclosed implants delivers sustained travoprost free acid levels through 4 months with drug depleted by 5 months. See e.g., FIG. 5. In addition, no statistically significant difference in central corneal thickness (CCT) was observed over 4 and 7 months. See e.g., FIGS. 3 and 4.

No changes in endothelial cell counts or pachymetry from baseline for certain subjects was observed through 9 months of treatment. See e.g., FIG. 9.

DETAILED DESCRIPTION

Figure 1:
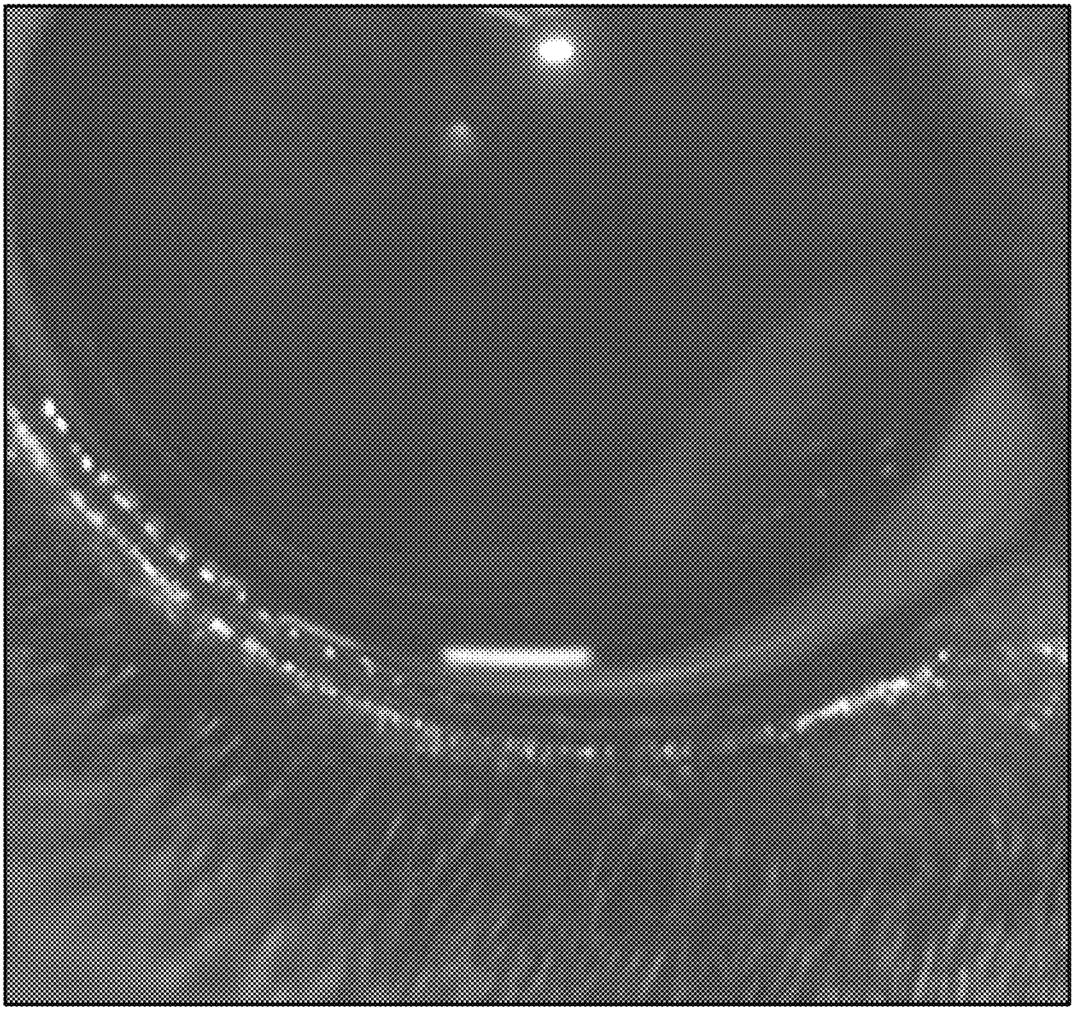
FIG. 1 shows fluorescein visualization of a disclosed implant at 3 days in vivo in beagles residing in the inferior iridocorneal angle using cobalt-blue light illumination through a yellow filter.

Provided herein are sustained release biodegradable hydrogel implants comprising travoprost and a polymer network.

Also provided herein are methods, uses, and medicament formulations for lowering ocular pressure in a subject, comprising administering to the eye of the subject a disclosed hydrogel implant.

Also provided herein are methods, uses, and medicament formulations for treating ocular hypertension in a subject, comprising administering to the eye of the subject a disclosed hydrogel implant.

Also provided herein are methods, uses, and medicament formulations for treating glaucoma in a subject, comprising administering to the eye of the subject a disclosed hydrogel implant.

1. Definitions

The term "biodegradable" refers to a material, such as the disclosed hydrogel implants, which degrades in vivo. Degradation of the material occurs over time and may occur concurrently with, or subsequent to, release of travoprost. In one aspect, "biodegradable" means that complete dissolution of the implant occurs, i.e., there is no residual hydrogel implant matter in the eye. In an alternative aspect, degradation may occur independently of travoprost release such that e.g., residual travoprost remains following degradation.

The term "polymer network" refers to a group of polymers comprising multiple branch structures (also referred to as "arms") cross-linked to other polymer chains. The polymer chains may be of the same or different chemical structures, e.g., as in complementary or non-complementary repeating units.

Nomenclature for synthetic precursors used to generate the disclosed polymer networks are referenced using the number of arms followed by the MW of the PEG and then the reactive group (e.g., electrophile or nucleophile). For example 4a20K PEG SAZ refers to a 20,000 Da PEG with 4 arms with a succinimidylazelate end group, 4a20K PEG SAP refers to a 20,000 Da PEG with 4 arms with a succinimidyladipate end group, 4a20K PEG SG refers to a 20,000 Da PEG with 4 arms with a succinimidylglutarate end group, 4a20K PEG SS refers to a 20,000 Da PEG with 4 arms with a succinimidylsuccinate end group, etc. Similarly, 4a20K PEG NH2 means a 20,000 Da PEG with 4 arms with an amine end group, 8a20K PEG NH2 means a 20,000 Da PEG with 8 arms with an amine end group, etc.

The term "semi-crystalline" refers to a polymer or polymer network which possesses some crystalline character, i.e., exhibits crystalline properties in thermal analysis, X-ray scattering or electron scattering experiments. In some aspects, "semi-crystalline" polymers or networks of polymers have a highly ordered molecular structure with sharp melt points. In some aspects, "semi-crystalline" polymers or networks of polymers do not gradually soften with a temperature increase and instead remain solid until a given quantity of heat is absorbed and then rapidly change into a rubber or liquid.

As used herein, "homogenously dispersed" means the component, such as the travoprost, is uniformly dispersed throughout the hydrogel or polymer network.

The term "treat", "treating", or "treatment" are used interchangeably and refer to reversing, alleviating, delaying the onset of, or inhibiting the progress of a disclosed condition (e.g., ocular hypertension or glaucoma), or one or more symptoms thereof, as described herein. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

It will be understood that the specific dosage and treatment regimen for any particular patient will depend upon a variety of factors, including the activity of the specific protein employed, the age, body weight, general health, sex, diet, time of administration, rate of excretion, the judgment of the treating physician and the severity of the particular condition being treated.

2. Implants

As part of a first embodiment, provided herein is a sustained release biodegradable intracameral hydrogel implant comprising travoprost and a polymer network.

As part of a second embodiment, the polymer network of the disclosed hydrogel implant (e.g., as in the first embodiment) comprises a plurality of polyethylene glycol (PEG) units.

As part of a third embodiment, the plurality of polyethylene glycol (PEG) units included in the disclosed implants are cross-linked to form a polymer network comprising a plurality of multi-arm PEG units having at least 2 arms, wherein the remaining features of the implants are described herein e.g., as in the first or second embodiment. Alternatively, as part of a third embodiment, the polymer network of the disclosed implants comprise a plurality of multi-arm PEG units having from 2 to 10 arms, wherein the remaining features of the implants are described herein e.g., as in the first or second embodiment. In another alternative, as part of a third embodiment, the polymer network of the disclosed implants comprise a plurality of multi-arm PEG units having from 4 to 8 arms, wherein the remaining features of the implants are described herein e.g., as in the first or second embodiment. In another alternative, as part of a third embodiment, the polymer network of the disclosed implants comprise a plurality of 4-arm PEG units, wherein the remaining features of the implants are described herein e.g., as in the first or second embodiment. In another alternative, as part of a third embodiment, the polymer network of the disclosed implants comprise a plurality of 8-arm PEG units, wherein the remaining features of the implants are described herein e.g., as in the first or second embodiment.

As part of a fourth embodiment, the polymer network of the disclosed implants comprises a plurality of PEG units having a number average molecular weight (Mn) ranging from about 5 KDa to about 50 KDa, wherein the remaining features of the implants are described herein e.g., as in the first through third embodiments. Alternatively, as part of a fourth embodiment, the polymer network of the disclosed implants comprise a plurality of PEG units having a number average molecular weight (Mn) ranging from about 5 KDa to about 40 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 5 KDa to about 30 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 10 KDa to about 50 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 10 KDa to about 40 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 10 KDa to about 30 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 10 KDa to about 20 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 30 KDa to about 50 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 35 KDa to about 45 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 15 KDa to about 30 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) ranging from about 15 KDa to about 25 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of at least about 5 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of at least about 10 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of at least 15 about KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of at least 20 about KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of at least 30 about KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of at least 40 about KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of about 10 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of about 15 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of about 20 KDa, wherein the remaining features of the implants are described herein e.g., as in the first through third embodiments. In another alternative, as part of a fourth embodiment, the polymer network of the disclosed implants comprise a plurality of PEG units having a number average molecular weight (Mn) of about 40 KDa, wherein the remaining features of the implants are described herein e.g., as in the first through third embodiments.

In a fifth embodiment, the polymer network of the disclosed implants comprise a plurality of PEG units crosslinked by a hydrolyzable linker, wherein the remaining features of the disclosed implants are described herein e.g., as in the first through fourth embodiments. Alternatively, as part of a fifth embodiment, the polymer network of the disclosed implants comprise a plurality of PEG units crosslinked by a hydrolyzable linker having the formula:

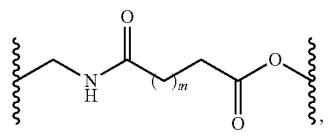

wherein m is an integer from 1 to 9 and wherein the remaining features of the implants are described herein e.g., as in the first through fourth embodiments. In another alternative, as part of a fifth embodiment, the polymer network of the disclosed implants comprise a plurality of PEG units crosslinked by a hydrolyzable linker having the formula:

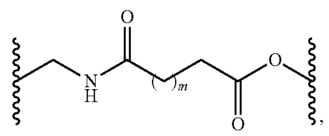

wherein m is an integer from 2 to 6 and wherein the remaining features of the implants are described herein e.g., as in the first through fourth embodiments. In another alternative, as part of a fifth embodiment, the polymer network of the disclosed implants comprise a plurality of PEG units having the formula:

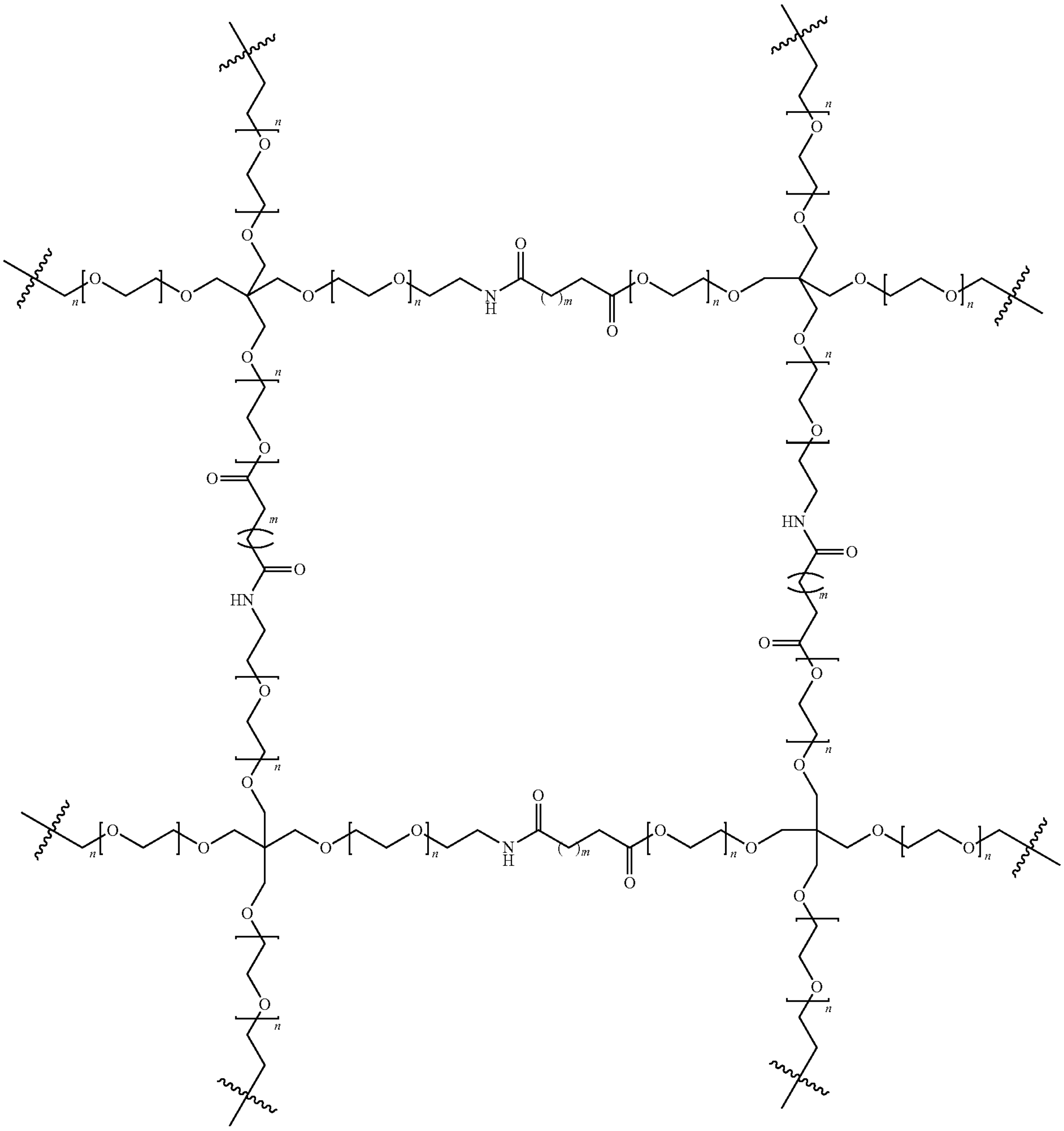

wherein n represents an ethylene oxide repeating unit and the wavy lines represent the points of repeating units of the polymer network, wherein the remaining features of the implants are described herein e.g., as in the first through fourth embodiments. In another alternative, as part of a fifth embodiment, the polymer network of the disclosed implants comprise a plurality of PEG units having the formula set forth above, but with an 8-arm PEG scaffold, wherein the remaining features of the implants are described herein e.g., as in the first through fourth embodiments.

In a sixth embodiment, the polymer network of the disclosed hydrogel implant is formed by reacting a plurality of polyethylene glycol (PEG) units comprising groups which are susceptible to nucleophilic attack with one or more nucleophilic groups to form the polymer network, wherein the remaining features of the hydrogel are described herein e.g., as in the first through fifth embodiments. Examples of suitable groups which are susceptible to nucleophilic attack include, but art not limited to activated esters (e.g., thioesters, succinimidyl esters, benzotriazolyl esters, esters of acrylic acids, and the like). Examples of suitable nucleophilic groups include, but art not limited to, amines and thiols.

In a seventh embodiment, the polymer network of the disclosed hydrogel implant is formed by reacting a plurality of polyethylene glycol (PEG) units, each having a molecule weight as described above in the fourth embodiment and which comprise groups which are susceptible to nucleophilic attack, with one or more nucleophilic groups to form the polymer network, wherein the remaining features of the hydrogel are described herein e.g., as in the first through sixth embodiments. Alternatively, as part of a seventh embodiment, the polymer network of the disclosed hydrogel implant is formed by reacting a plurality of polyethylene glycol (PEG) units, each having a molecule weight as described above in the fourth embodiment and which comprise a succinimidyl ester group, with one or more nucleophilic groups to form the polymer network, wherein the remaining features of the hydrogel are described herein e.g., as in the first through sixth embodiments. In another alternative, as part of a seventh embodiment, the polymer network of the disclosed hydrogel implant is formed by reacting a plurality of polyethylene glycol (PEG) units selected from 4a20K PEG SAZ, 4a20K PEG SAP. 4a20K PEG SG, 4a20K PEG SS, 8a20K PEG SAZ, 8a20K PEG SAP. 8a20K PEG SG, 8a20K PEG SS, wherein the remaining features of the hydrogel are described herein e.g., as in the first through sixth embodiments.

In an eighth embodiment, the polymer network of the disclosed hydrogel implant is formed by reacting a plurality of polyethylene glycol (PEG) units comprising groups which are susceptible to nucleophilic attack with one or more amine groups to form the polymer network, wherein the remaining features of the hydrogel are described herein e.g., as in the first through seventh embodiments. Alternatively, as part of a sixteenth embodiment, the polymer network of the disclosed hydrogel implant is formed by reacting a plurality of polyethylene glycol (PEG) units comprising groups which are susceptible to nucleophilic attack with one or more PEG or Lysine based-amine groups to form the polymer network, wherein the remaining features of the hydrogel are described herein e.g., as in the first through seventh embodiments. In another alternative, as part of a sixteenth embodiment, the polymer network of the disclosed hydrogel implant is formed by reacting a plurality of polyethylene glycol (PEG) units comprising groups which are susceptible to nucleophilic attack with one or more PEG or Lysine based-amine groups selected from 4a20K PEG NH2, 8a20K PEG NH2, and trilysine, or salts thereof, wherein the remaining features of the hydrogel are described herein e.g., as in the first through seventh embodiments.

As part of a ninth embodiment, the polymer network of the disclosed implants are amorphous (e.g., under aqueous conditions such as in vivo), wherein the remaining features of the implants are described herein e.g., as in the first through eighth embodiments. Alternatively, as part of a ninth embodiment, the polymer network of the disclosed implants are semi-crystalline (e.g., in the absence of water), wherein the remaining features of the compositions are described herein e.g., as in the first through eighth embodiments.

As part of a tenth embodiment, the travoprost of the disclosed implants is homogenously dispersed within the polymer network, wherein the remaining features of the implants are described herein e.g., as in the first through ninth embodiments.

As part of an eleventh embodiment, the travoprost is delivered to the eye in a sustained manner for a period ranging from about 1 month to about 1 year, wherein the remaining features of the implants are described herein e.g., as in the first through tenth embodiments. Alternatively, as part of an eleventh embodiment, the travoprost is delivered to the eye in a sustained manner for a period ranging from about 1 month to about 11 months, wherein the remaining features of the implants are described herein e.g., as in the first through tenth embodiments. In another alternative, as part of an eleventh embodiment, the travoprost is delivered to the eye in a sustained manner for a period ranging from about 1 month to about 10 months, wherein the remaining features of the implants are described herein e.g., as in the first through tenth embodiments. In another alternative, as part of an eleventh embodiment, the travoprost is delivered to the eye in a sustained manner for a period ranging from about 1 month to about 9 months, wherein the remaining features of the implants are described herein e.g., as in the first through tenth embodiments. In another alternative, as part of an eleventh embodiment, the travoprost is delivered to the eye in a sustained manner for a period ranging from about 1 month to about 8 months, wherein the remaining features of the implants are described herein e.g., as in the first through tenth embodiments. In another alternative, as part of an eleventh embodiment, the travoprost is delivered to the eye in a sustained manner for a period ranging from about 2 month to about 8 months, wherein the remaining features of the implants are described herein e.g., as in the first through tenth embodiments. In another alternative, as part of an eleventh embodiment, the travoprost is delivered to the eye in a sustained manner for a period ranging from about 3 month to about 7 months, wherein the remaining features of the implants are described herein e.g., as in the first through tenth embodiments. In another alternative, as part of an eleventh embodiment, the travoprost is delivered to the eye in a sustained manner for a period ranging from about 4 month to about 6 months, wherein the remaining features of the implants are described herein e.g., as in the first through tenth embodiments. In another alternative, as part of an eleventh embodiment, the travoprost is delivered to the eye in a sustained manner for a period of about 1 month, wherein the remaining features of the implants are described herein e.g., as in the first through tenth embodiments. In another alternative, as part of an eleventh embodiment, the travoprost is delivered to the eye in a sustained manner for a period of about 2 months, wherein the remaining features of the implants are described herein e.g., as in the first through tenth embodiments. In another alternative, as part of an eleventh embodiment, the travoprost is delivered to the eye in a sustained manner for a period of about 3 months, wherein the remaining features of the implants are described herein e.g., as in the first through tenth embodiments. In another alternative, as part of an eleventh embodiment, the travoprost is delivered to the eye in a sustained manner for a period of about 4 months, wherein the remaining features of the implants are described herein e.g., as in the first through tenth embodiments. In another alternative, as part of an eleventh embodiment, the travoprost is delivered to the eye in a sustained manner for a period of about 5 months, wherein the remaining features of the implants are described herein e.g., as in the first through tenth embodiments. In another alternative, as part of an eleventh embodiment, the travoprost is delivered to the eye in a sustained manner for a period of about 6 months, wherein the remaining features of the implants are described herein e.g., as in the first through tenth embodiments.

As part of a twelfth embodiment, sustained release of the travoprost occurs in the aqueous humor, wherein the remaining features of the implants are described herein e.g., as in the first through eleventh embodiments.

As part of a twelfth embodiment, travoprost in the disclosed implants is microencapsulated, wherein the remaining features of the implants are described herein e.g., as in the first through eleventh embodiments. Alternatively, as part of a twelfth embodiment, travoprost in the disclosed implants is microencapsulated with poly(lactic-co-glycolic acid) (PLGA) or poly(lactic acid) (PLA), or a combination thereof, wherein the remaining features of the implants are described herein e.g., as in the first through eleventh embodiments. In another alternative, as part of a twelfth embodiment, travoprost in the disclosed implants is microencapsulated with PLA, wherein the remaining features of the implants are described herein e.g., as in the first through eleventh embodiments.

As part of an thirteenth embodiment, the polymer network of the disclosed hydrogel implants is conjugated to fluorescein, wherein the remaining features of the implants are described herein e.g., as in the first through twelfth embodiments.

As part of a fourteenth embodiment, the disclosed implants are designed for implantation near the corneal endothelial cells, wherein the remaining features of the implants are described herein e.g., as in the first through thirteenth embodiments.

As part of a fifteenth embodiment, the disclosed implants are designed for implantation in the inferior iridocorneal angle, wherein the remaining features of the implants are described herein e.g., as in the first through fourteenth embodiments.

As part of a sixteenth embodiment, the disclosed implants comprise 5 μg, 15 μg or 26 μg of travoprost, wherein the remaining features of the implants are described herein e.g., as in the first through fifteenth embodiments. Alternatively, as part of a the disclosed implants comprise 5 μg, 15 μg or 26 μg of travoprost; and comprises a polymer networks formed by reacting a plurality of polyethylene glycol (PEG) units comprising groups which are susceptible to nucleophilic attack with one or more PEG or Lysine based-amine groups selected from 4a20K PEG NH2, 8a20K PEG NH2, and trilysine, wherein the remaining features of the hydrogel are described herein e.g., as in the first through seventh embodiments.

As part of a seventeenth embodiment, the disclosed implants are fully degraded following complete release of travoprost, wherein the remaining features of the implants are described herein e.g., as in the first through fifteenth embodiments. Alternatively, as part of a seventeenth embodiment, the hydrogel implant is fully degraded after about 12 months, after about 11 months, after about 10 months, after about 9 months, after about 8 months, after about 6 months, after about 5 months, after about 4 months, after about 3 months, after about 2 months, after about 1 month (i.e., after about 30 days) following complete release of travoprost, wherein the remaining features of the implants are described herein e.g., as in the first through fifteenth embodiments. Alternatively, as part of a seventeenth embodiment, the hydrogel implant is fully degraded following at least 90% (e.g., at least 91%, at least 92%, at least 93%, at least 94%, at least 95%, at least 96%, at least 97%, at least 98%, or at least 99%) release of travoprost, wherein the remaining features of the implants are described herein e.g., as in the first through fifteenth embodiments.

Methods and Uses

The disclosed implants are useful in lowering ocular pressure. Thus, provided herein are methods of lowering ocular pressure in a subject in need thereof comprising administering a hydrogel implant described herein. Also disclosed in the use of a disclosed implant for lowering ocular pressure in a subject. Further provided is the use of a disclosed implant in the manufacture of a medicament for lowering ocular pressure.

Also provided are methods of treating ocular hypertension in a subject in need thereof comprising administering a hydrogel implant described herein. Also disclosed in the use of a disclosed implant for treating ocular hypertension in a subject. Further provided is the use of a disclosed implant in the manufacture of a medicament for treating ocular hypertension.

Also provided are methods for treating glaucoma (open angle glaucoma) in a subject in need thereof comprising administering a hydrogel implant described herein. Also disclosed in the use of a disclosed implant for treating glaucoma (open angle glaucoma) in a subject. Further provided is the use of a disclosed implant in the manufacture of a medicament for treating glaucoma (open angle glaucoma).

EXEMPLIFICATION

The present invention will now be illustrated by the following non-limiting examples.

Synthetic Methods

Intracameral Depot comprises travoprost as the active pharmaceutical ingredient (API), polylactide (PLA) microparticles which provide sustained delivery of the API and 8-arm polyethylene glycol (PEG) based hydrogel conjugated with fluorescein which serves as the inactive delivery platform.

Microparticle Encapsulation

| Step | Manufacturing Action |
|---|---|
| 1 | Prepare Polyvinyl Alcohol (PVA) stock solution in water. |
| 2 | Prepare dispersed phase (DP) by dissolving travoprost and PLA in dichloromethane (DCM). |
| 3 | Prepare continuous phase (CP) by diluting the PVA stock solution with water in a reactor and mix using an overhead mixer. Prepare CP with DCM in a separate reactor if required (for 4A, 7A, 9A, 5.5E PLA). |
| 4 | Inject the travoprost/PLA solution (DP) at the inlet of the homogenizer through a cannula positioned perpendicular to the flow of the continuous phase. After homogenization, the nascent microparticles flow into the quench reactor. |
| 5 | Mix the suspension in quench reactor for 16-24 hours to allow evaporation of DCM and harden microparticles. |
| 6 | After hardening, transfer microparticles from the outlet of the quench reactor to the inlet of the sieve agitator using a peristaltic pump. |
| 7 | Agitate microparticles on the sieve stack at a set rate while/washing with a continuous flow of water. Through this process the microparticles are sieved to the specified size fractions. |
| 8 | Aliquot the wet sieved microparticles into vials, remove excess water from the vials and freeze dry. |
| 9 | Store dry microparticles frozen until ready for depot fabrication. |

Intracameral Implant Manufacturing

| Step | Manufacturing Action |
|---|---|
| 1 | Cut polyurethane tubing in appropriate length pieces and insert dispensing tips to both ends of the tubing pieces. |
| 2 | Formulate Trilysine Acetate (TLA)/NHS Fluorescein (FL) solution and allow to react for 1-24 hours. |
| 3 | Formulate PEG solution, microparticle suspension and aliquot appropriate amount of TLA/FL solution in three different syringes to cast a single run of depots. The OTX-TIC Intracameral Depot process is designed to build four separate runs and pool them together in a single batch. |
| 4 | Combine content of three syringes (PEG/Microparticles/TLA-FL) and inject through the dispensing tip into tubing pieces. Cap the |

-continued

| Intracameral Implant Manufacturing | |
|---|---|
| Step | Manufacturing Action |
| | dispensing tips to close the tubing. Roll the tubing strands while gel sets. Measure and record the gel time. Repeat for each run. |
| 5 | After gel has formed, place strands on drying fixtures and dry in an incubator. |
| 6 | Remove the dry hydrogel strands from the drying fixture and cut into 2.0 mm long implants. |
| 7 | Inspect each implant under the microscope for the in-process visual, length and diameter specifications. Discard any depots outside of the specification. |

| Intracameral Depot Packaging and Yield Calculations | |
|---|---|
| Step | Manufacturing Action |
| 1 | Prepare syringe assemblies, package in foil pouches and sterilize. |
| 2 | Attach a needle to the pre-sterilized syringe assembly and poke a hole through the luer hub of the needle. |
| 3 | Cut an appropriate size wire and feed it into the tip of the needle. Ensure the wire is flush with the tip of the needle. Withdraw the plunger and ensure the wire sits on top of the plunger in upright position. Clip the syringe lock onto the plunger. |
| 4 | Insert a single implant into the needle. Insert a second piece of wire into the tip of the wire. Place the protective cap on the needle. |
| 5 | Place the syringe kit assembly in the foil pouch with the needle cap oriented away from the opening of the foil pouch. Repeat steps 2-5 for all syringe assemblies to be packaged. |
| 6 | Transfer foil pouches into the glove box and allow foil pouches containing depots in syringe assemblies to condition for 24-96 hours. |
| 7 | Seal foil pouches and remove from the glove box. |
| 8 | Transfer the sealed foil pouches in clearly labeled bags and store in a refrigerator prior to sterilization. |
| 9 | Complete required yield calculations. |

Figure 5:
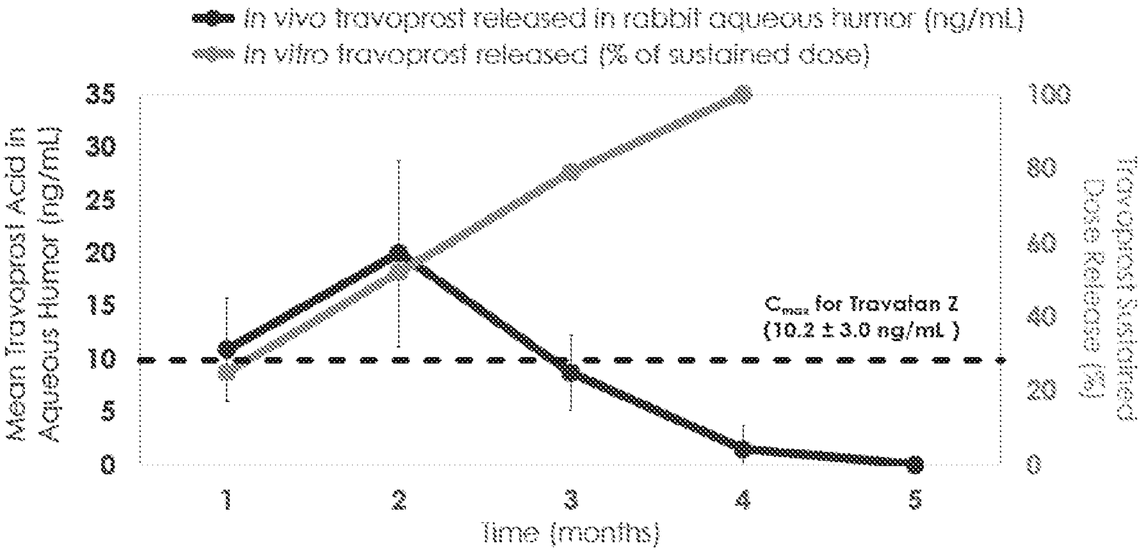
FIG. 5 shows the pharmacokinetics of travoprost released from a disclosed implant in vivo (rabbits) and in vitro over 5 months.

Example 1: Pharmacokinetic Release of Travoprost Using an Inventive Hydrogel Implant An intracameral implant comprising travoprost particles formulated into a hydrogel matrix was injected into the anterior chamber bilaterally (N=48) through a 27 gauge needle in 24 New Zealand White rabbits on Day 0. In vivo drug release was assessed by collecting aqueous humor samples from 6 eyes at Days 34 and 63, and 12 eyes at Days 91, 126 and 153. Drug concentrations in the aqueous humor were measured by LC/MS/MS. In vitro drug release was assessed in physiologically representative conditions (PBS with a surfactant (polyoxyl hydrogenated castor oil 40), pH 7.4, 37° C.) at Days 28, 63, 92, 119, and 126, and analyzed by UPLC/UV. Pharmacokinetic findings are shown below and in Table 1 and FIG. 5.

TABLE 1

| In Vivo (Rabbit AH) | | OS mean ± SD | In Vitro (PBS, pH 7.4, 37° C.) | |
|---|---|---|---|---|
| | | | | Travoprost |
| Time (months) | OD Time (days) | travoprost acid (ng/mL) | Time (days) | released (% of sustained dose) |
| 1 | 34 | 10.9 ± 4.9 | 28 | 25% |
| 2 | 63 | 20.0 ± 8.8 | 63 | 52% |
| 3 | 91 | 8.7 ± 3.5 | 92 | 79% |
| 4 | 126 | 1.5 ± 2.2 | 119-126 | 100% |
| 5 | 153 | 0.0 ± 0.0 | NA | NA |
| Comparison with Maximum Travoprost free acid Concentration from a single drop administration | | | | |
| Travoprost Z at 1 hour | | 10.2 ± 3.0 | NA | NA |

Aqueous humor sample in rabbits demonstrated elevated travoprost free acid level post-injection through 3-4 months and an absence at 5 months. The inventive implant released approximately 25% of the travoprost sustained dose in vitro each month for 4 months. The decrease in travoprost free acid concentration observed at 4 months aligns with the decrease in in vitro release rate observed at 4 months. The inventive implant drug concentrations of 10.9, 20.0, and 8.7 ng/mL at 1, 2, and 3 months are comparable to or exceed the maximum travoprost free acid concentration of 10.2±3.0 ng/mL from a single drop administration of Travoprost Z (travoprost solution/drops Alcon laboratories) in rabbits at 1 hour, as reported in the literature (Travatan Z NDA 21-994). Longer release durations (e.g., >6 months) are projected in humans compared to rabbits due to lower anterior chamber temperatures and reduced pH slowing hydrolysis of the biodegradable particles within the inventive implant.

Example 2: Inventive Hydrogel Implants Effects on Central Corneal Thickness

Figure 2:
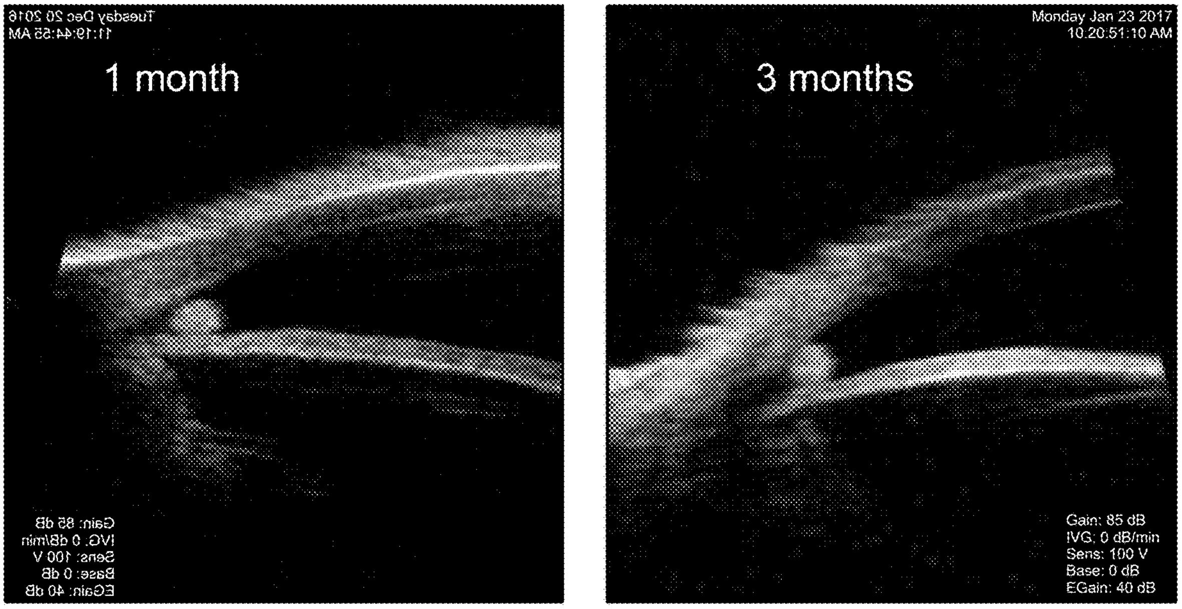
FIG. 2 shows ultrasound images in beagles of a disclosed implant residing in the iridocorneal angle at 1 month and 3 months after injection.

Studies were performed in beagle dogs to report central corneal thickness (CCT). Inventive hydrogel implant, containing 18 μg travoprost per implant and designed to degrade over time providing sustained release of travoprost over 4-6 months, was injected via a 27 gauge needle into the lower portion of the anterior chamber on Day 0 (Table 2), where the implant resides in the iridocorneal angle. Five individual pachymetry measurements were obtained per eye and averaged together to report a mean CCT and standard deviation per time point. Both implant treated eyes were averaged per animal (Study 1: OD (n=6) and OS (n=6); Study 2: OD (n=8) and OS (n=8)). Fluorescein visualization with a cobalt-blue light illumination though a yellow filter was performed at 3 days showing the implant residing in the inferior iridocorneal angle (FIG. 1). Ultrasound images in beagles showing the implant residing in the iridocorneal angle at 1 month and 3 months after injection is shown in FIG. 2.

TABLE 2

| Study | Duration (months) | N | Treatment on Day 0 OD | OS | Pachymetry Time-points | Pachymetry Device Used |
|---|---|---|---|---|---|---|
| 1 | 7 | 12 | Inventive Implant | | Baseline & months 0.5, 1-7 | Ultrasound Pachymeter |
| 2 | 4 | 8 | Untreated (no implant) | Vehicle Control (no drug) | Baseline & months 0.5, 1-7 | Ultrasound Pachymeter |
| | | 16 | Inventive Implant | | | |

Figure 3:
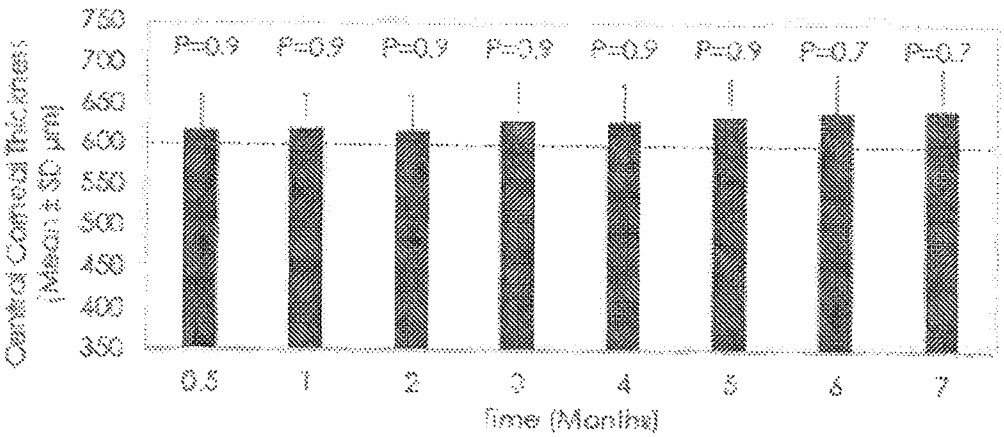
FIG. 3 shows the central corneal thickness pre- and post-administration of a disclosed implant in beagles demonstrating no significant change over 7 months compared to baseline.
Figure 4:
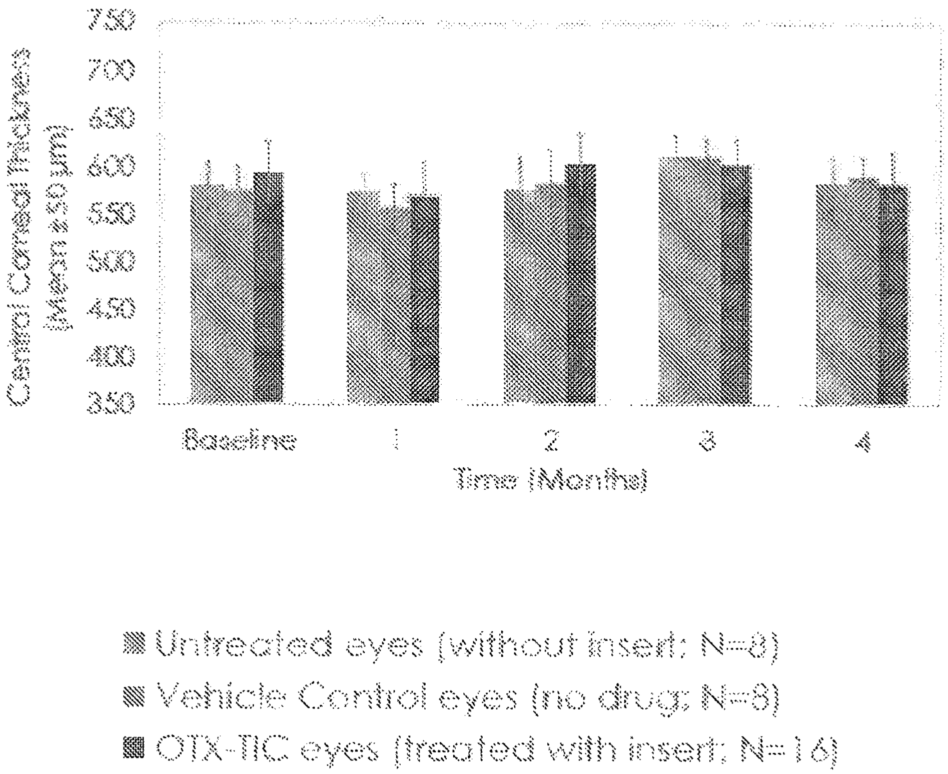
FIG. 4 shows the central corneal thickness pre- and post-administration of a disclosed implant in beagle eyes demonstrating no significant change over 4 months.

Administration into the anterior chamber of beagle eyes demonstrated no statistically significant differences in CCT (one-way ANOVA with post-hoc tukey test P≥0.05) over 7 months (FIG. 3). Baseline CCT was 596±μm. It was also found that there was no statistically significant difference (P≥0.05) in CCT measured in implanted eyes over 4 months when compared to either untreated or vehicle control eyes in beagles (FIG. 4).

Example 3—Pharmacokinetics a. Pharmacokinetics in Dogs Administered Inventive (Travoprost) Implant—PK Study The purpose of the study was to inject the inventive hydrogel implant containing either 5 μg, 15 μg or 26 μg of the active ingredient travoprost into the anterior chamber of beagle dogs and collect aqueous humor and plasma samples over time to assess the travoprost and travoprost free acid pharmacokinetic profile using the same batch of hydrogel test articles containing 18 μg of travoprost per implant that was assessed in the 120-day Intracameral Ocular Toxicity Study in Beagle Dogs. A secondary assessment for pharmacodynamic evaluation measured the intraocular pressure and pupil diameter over the study duration. A safety evaluation included daily clinical observations and daily ocular irritation assessments over the study duration.

Drug levels of travoprost (prodrug ester) and travoprost free acid (active) in plasma and aqueous humor (AH) released from inventive hydrogel were determined in beagles over 4 months to generate pharmacokinetic profiles. For aqueous humor (via paracentesis) and plasma sampling the 12 animals were divided into 4 groups with 3 animals (n=6 eyes) per group in the following manner: Group 1 (Pre-Dose; Weeks 2, 10); Group 2 (1 hour Post Dose; Weeks 4, 12); Group 3 (4 hours Post Dose; Weeks 6, 14); and Group 4 (1 Day Post Dose; Weeks 8, 16). Sample analysis was performed using a validated LC-MS/MS assay method.

All travoprost (LOQ=0.5 ng/ml) and travoprost free acid (LOQ=0.25 ng/ml) plasma values were reported to be below the limit of quantitation (LOQ). This result below the LOQ in plasma was anticipated since the travoprost sustained release dose from the implant is primarily delivered over a period of 4-months into the systemic system. Additionally it was shown previously that plasma concentrations below the LOQ (LOQ=0.01 ng/mL) are generally observed following topical ocular dosing of TRAVATAN (travoprost ophthalmic solution) 0.004%, with no demonstration of accumulation.

Travoprost and travoprost free acid concentrations were measured in beagle AH that were collected pre-dose and post-dose (1 and 4 hours, and at 2, 4, 6, 8, 10, 12, 14 and 16 weeks) to determine pharmacokinetics of drug levels in AH. The LOQ for this method is 0.05 ng/ml and values less than the LOQ are reported as zero. Test results are presented in Table 3. The $T_{max}$ for travoprost occurs 1 hour post dose with a reported mean $C_{max}$ of 68.7 ng/mL. The $T_{max}$ for travoprost free acid occurs 4 hours post dose with a reported mean $C_{max}$ of 16.7 ng/mL. The TFA levels in beagles were an average of 1.4 ng/ml (range 0.3 to 4.2 ng/mL) for the 18 μg dosage strength from Days 1 to 112.

TABLE 3

Ocular Pharmacokinetic/Toxicokinetic Study Summary for Travoprost and Travoprost Free Acid in the Aqueous Humor of Beagle Dogs Following Intracameral Administration of OTX-TIC

| | Travoprost (ng/mL) | | Travoprost Free Acid (ng/mL) | |
|---|---|---|---|---|
| Time | Mean (n = 6 eyes) | Standard Deviation | Mean (n = 6 eyes) | Standard Deviation |
| Pre-dose | 0.0 | 0.0 | 0.0 | 0.0 |
| 1 hour | 68.7 | 39.8 | 6.5 | 5.0 |
| 4 hours | 26.1 | 23.8 | 16.7 | 13.1 |
| 1 day | 13.5 | 10.0 | 2.3 | 2.7 |
| 14 days | 0.6 | 0.7 | 0.8 | 0.9 |
| 28 days | 0.1 | 0.2 | 4.2 | 1.7 |
| 42 days | 0.1 | 0.1 | 1.1 | 0.4 |
| 56 days | 0.0 | 0.0 | 0.3 | 0.3 |
| 70 days | 0.0 | 0.1 | 2.0 | 2.1 |
| 84 days | 0.0 | 0.0 | 1.3 | 1.2 |
| 98 days | 0.0 | 0.0 | 0.3 | 0.2 |
| 112 days | 0.0 | 0.0 | 0.3 | 0.4 |
| $T_{max}$ | 1 hour | n.a. | 4 hours | n.a. |
| $C_{max}$ | 68.7 | 39.8 | 16.7 | 13.1 |

Figure 6:
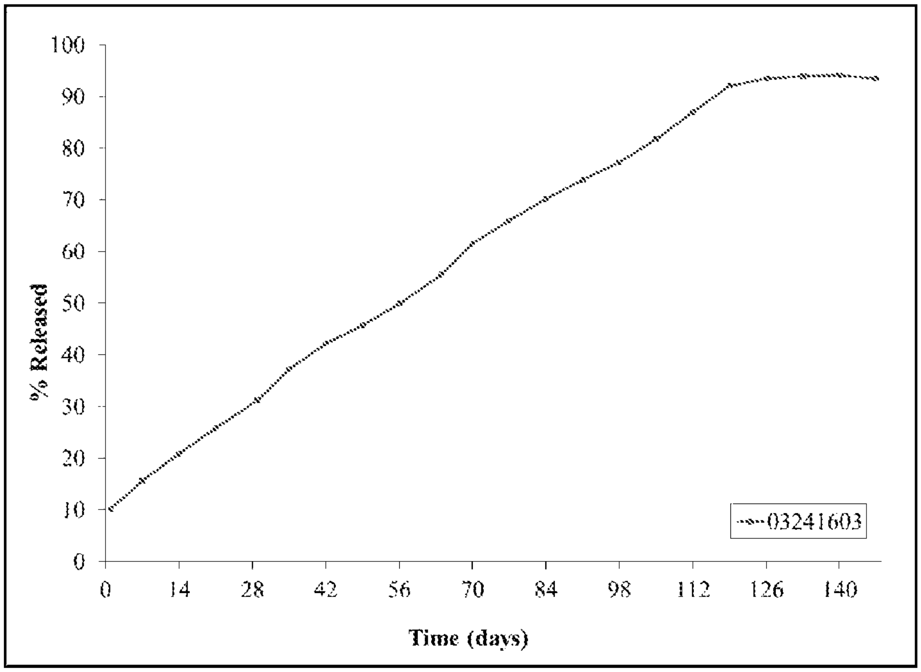
FIG. 6 shows in vitro release testing of an inventive implant over 147 days.

The $T_{max}$ aligns with the in vitro burst release from inventive implant, which occurs within 1 day of dissolution testing in release media. Steady state drug release (zero-order kinetics) from inventive implant is observed from Day 1 through 4 months during dissolution testing in release media, as seen in FIG. 6. The in vitro release of the test articles studied was performed in biorelevant conditions that utilized a dissolution media of 1×PBS, 0.5% polyoxyl 40 hydrogenated castor oil, 0.01% sodium fluoride, pH 7.2-7.4 performed at 37° C. The polyoxyl 40 hydrogenated castor oil is added as a nonionic surfactant to aid travoprost solubility to ensure sink conditions and it is used for this purpose to aid solubility in commercial Travatan® eye drop formulations. Because of the duration of the release test, sodium fluoride is added as a bacteriostatic agent to the release media. The basis of travoprost release from inventive implant is the degradation of the PLA microparticles to lower molecular weights by ester hydrolysis in the presence of water and the subsequent release of the entrapped travoprost from within the microparticles.

b. Pharmacokinetics in Dogs Administered Inventive (Travoprost) Implant—Dose Response PK/PD/Persistence/Tolerability Study The purpose of this study was to investigate aqueous humor pharmacokinetics, pharmacodynamics (intraocular pressure "IOP" and pupil diameter "PD"), implant persistence, implant location with imaging, and eye tolerability after a single anterior chamber (intracameral) injection of inventive implant comprising travoprost in male beagle dogs over a 7-month period at two dosage strengths. Inventive implant containing 14 μg or 41 μg travoprost per implant was administered via intracameral injection in 12 normotensive beagles (n=6 beagles/12 eyes per dosage strength). This section will discuss the pharmacokinetic portion of this study.

Drug levels of travoprost (prodrug ester) and travoprost free acid (active) in aqueous humor (AH) released from inventive implant were determined in beagles over the study duration to generate pharmacokinetic profiles. For aqueous humor sampling via paracentesis the 12 animals were divided into 4 groups with 3 animals (n=6 eyes) per group in the following manner: Low Dose—Group 1 (Days 29, 92, 148, 211 OU eyes); Low Dose—Group 2 (Pre-Dose OD eyes, Days 59, 120, 183 OU eyes); High Dose—Group 3

(Days 29, 92, 148, 211 OU eyes); and High Dose—Group 4 (Pre-Dose OD eyes, Days 59, 120, 183 OU eyes). Sample analysis was performed using a validated LC-MS/MS assay method. The LOQ for this method is 0.050 ng/mL and values less than the LOQ are reported as zero.

Figure 7:
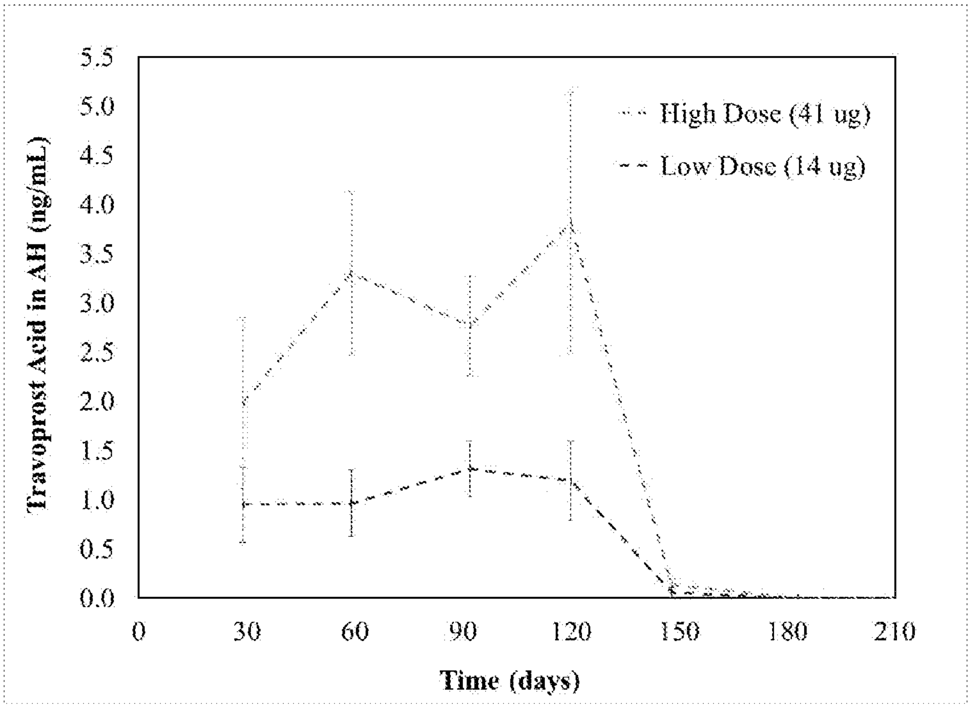
FIG. 7 shows the pharmacokinetics for travoprost free acid in the aqueous humor of beagle dogs following low and high dose administration of an inventive implant.

Travoprost and travoprost free acid (TFA) concentrations were measured as <LOQ for all pre-dose AH samples. The travoprost ester form in the AH was <LOQ for all study timepoints and only TFA levels above the LOQ were observed. It has been demonstrated that travoprost released from a sustained released intracameral depot converts to the active travoprost free acid form in the aqueous humor within the anterior chamber of normotensive beagle eyes. The mean TFA results for both dosage strengths are presented in FIG. 7. Results demonstrate an average TFA concentration with standard deviations in the beagle AH of 1.1±0.2 ng/mL for the low dosage strength and 3.0±0.8 ng/mL for the high dosage strength through 120 days. Following 120 days the values drop to 0.1 ng/mL for both dosage strengths and then are below the LOQ for the remainder of the study.

Figure 8:
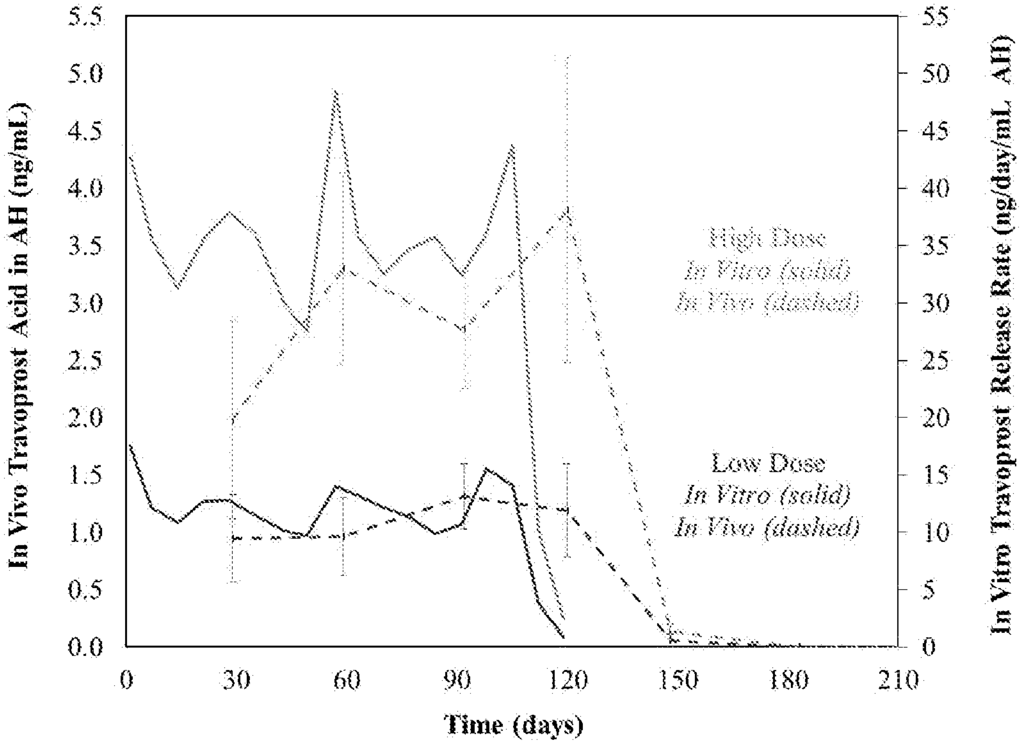
FIG. 8 shows a comparison of travoprost free acid in the aqueous humor of beagle dogs compared to the theoretical maximal concentration from in vitro release testing.

A comparison between the travoprost concentrations released in vitro was made to the concentrations measured in vivo in the beagle AH over the study duration. The amount of travoprost released from the test articles in vitro was converted to daily concentrations by determining the daily amount of travoprost mass released between sampling points in vitro divided by the aqueous humor daily flow rate in beagles (8.5 mL/day). For a comparable in vitro and in vivo hydrolytic degradation rate the in vitro value approximates the theoretical maximal concentration of cumulative travoprost and/or TFA in the beagle AH. This is plotted on the right side y-axis in FIG. 8 and compared to the PK profiles previously presented in FIG. 6 for the low- and high dose formulations. Results demonstrate an approximate 10-fold difference in concentration for both dosage strengths between the in vivo TFA levels and the in vitro cumulative travoprost levels over the study duration. This is an early demonstration of an in vitro/in vivo relationship, showing an approximate bioavailability of 10% in an animal model that is maintained over the study duration at two different dosage strengths. The remaining 90% of released travoprost most likely passes directly into outflow pathways due to close proximity in the inferior angle. A dose relationship is established since the 3× difference in TFA concentrations in the AH correlates with the 3× difference in dose between the low (14 μg) and high (41 μg) strengths assessed in this study.

Example 4—Pharmacology a. Repeat Low Dose Administration in Lasered Hypertensive Cynomolgus Monkeys A Travatan® eye drop is a 25 uL drop size at 40 μg/mL or 1 μg per drop and it is administered once per day. A single and twice a day dose of 0.3 μg travoprost has been demonstrated to reduce IOP by 19-26% and 19%-30% in lasered hypertensive cynomolgus monkeys, respectively. A single dose of 0.1 μg travoprost did not significantly lower IOP, however continued twice a day dosing at 0.1 μg resulted in significant lowering of IOP after doses 4 and 5 (Travatan NDA 021257 Pharmacology Review). This IOP reduction observed in the monkey with more frequent low dose delivery of travoprost augments the basis for efficacy via sustained drug delivery from the inventive (travoprost) implant.

b. IOP Reduction and Effects on Pupil Diameter in Dogs with Travatan® Eye Drops

Figure 9:
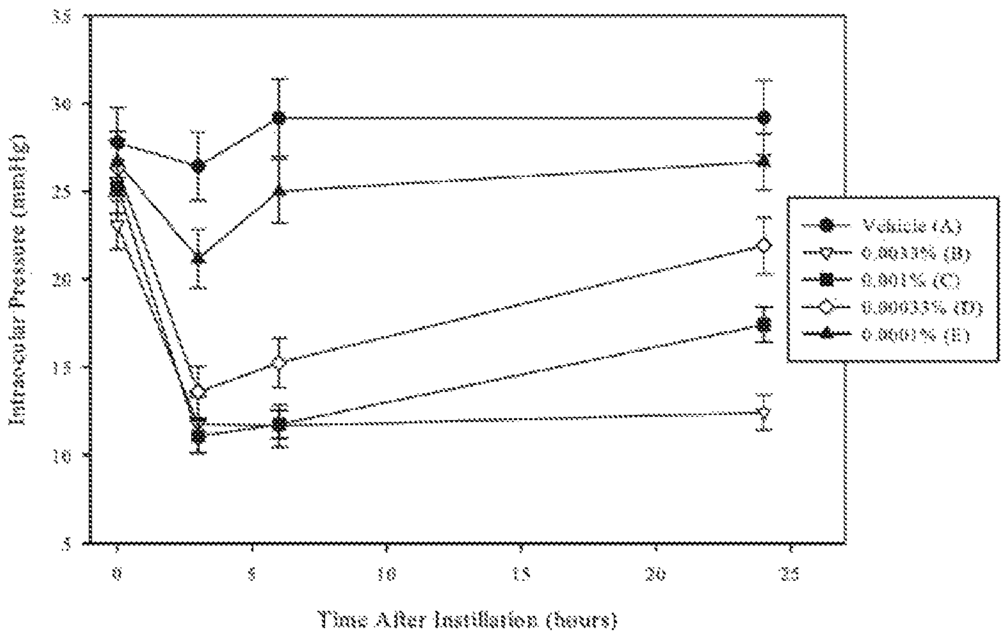
FIG. 9 shows the effect of selected concentrations of travoprost in beagles with primary open angle glaucoma on IOP.
Figure 10:
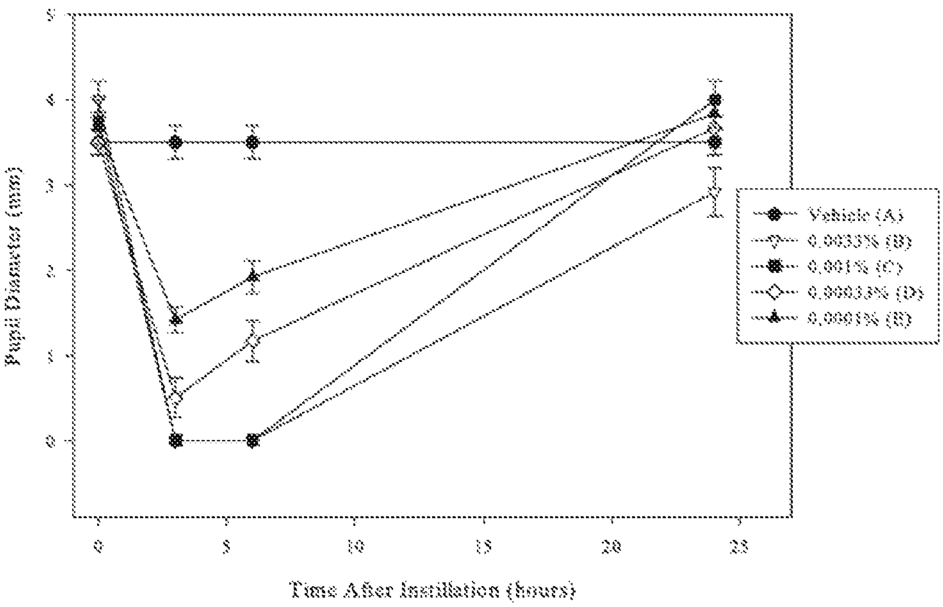
FIG. 10 shows the effect of selected concentrations of travoprost on pupil diameter in beagles with primary open angle glaucoma.

A pharmacodynamic study performed in twelve glaucomatous beagles evaluated the changes in intraocular pressure (IOP) and pupil diameter (PD) after instillations of 0.033, 0.0033, 0.001, 0.00033, and 0.0001% travoprost in multiple single-dose studies. Concentrations of 0.00033, 0.001, and 0.0033% travoprost significantly lowered IOP (see FIG. 9) and PD (see FIG. 10), but the 0.0001% concentration provided limited IOP changes, although PD changes were still significant. This suggests travoprost is effective in the dog to lower IOP and reduce pupil size at concentrations starting between 0.0001 and 0.00033% (1/12 the commercially available concentration). However, only the ≥0.001% travoprost dosage strength maintained IOP reduction for 24 hours and no dosage strength maintained pupil constriction for 24 hours.

c. IOP Reduction in Dogs with a Travoprost Intracameral Implant

A pharmacodynamic study of a biodegradable travoprost sustained release implant that was administered via intracameral injection in 3 beagle dogs (n=6 eyes) was reported in the literature (Robeson, RiLee, et al. "A 12-Month Study of the ENV515 (Travoprost) Intracameral Implant on Intraocular Pressure in Beagle Dogs." Investigative Ophthalmology & Visual Science 58.8 (2017): 1072-1072). An IOP reduction was observed for 7-months with an average treatment effect of a 38% decrease in IOP from baseline. No dosing information was reported in this study.

d. IOP Reduction and Effects on Pupil Diameter in Dogs with Inventive (Travoprost) Implant—PK Study The purpose of the study was to inject inventive implant into the anterior chamber of beagle dogs and collect aqueous humor and plasma samples over time to assess the travoprost and travoprost free acid pharmacokinetic profile using the same batch of inventive implant test articles containing 18 μg of travoprost per implant that was assessed in the 120-day Intracameral Ocular Toxicity Study in Beagle Dogs. A secondary assessment for pharmacodynamic evaluation measured the intraocular pressure and pupil diameter over the study duration is discussed in this section. A safety evaluation included daily clinical observations and daily ocular irritation assessments over the study duration.

Inventive implant containing 18 μg travoprost per implant was administered via intracameral injection into both eyes of 12 normotensive beagles (n=24 eyes). Intraocular pressure was measured using a TonoVet® tonometer and pupil diameter was measured using a standard commercial ruler with both measurements done pre- and monthly post-dose administration.

The IOP measurements taken pre- and post-administration of inventive implant are presented in Table 4. All animals received the same inventive implant test article and were divided into four groups for pharmacokinetic sampling purposes. Results demonstrate a mean baseline of IOP of 19 mmHg followed by an IOP reduction to 11 mmHg (−42%) at 1 month, 13 mmHg (−32%) at 2-months, 12 mmHg (−37%) at 3-months and 15 mmHg (−21%) at 4 months demonstrating the intended primary pharmacodynamic response of IOP reduction post administration over the study duration.

TABLE 4

Pre- and Post- Inventive Implant Administration Intraocular Pressure Measurements over the Study Duration.

| | | Month Number Relative to Start Date | | | | | | | | | |
|---|---|---|---|---|---|---|---|---|---|---|---|
| | Animal | Pre-Dose | | Month 1 | | Month 2 | | Month 3 | | Month 4 | |
| Group # | # | R | L | R | L | R | L | R | L | R | L |
| Group 1 | 1101 | 21 | 16 | 7 | 8 | 11 | 11 | 12 | 11 | 19 | 17 |
| | 1102 | 25 | 21 | 7 | 11 | 13 | 14 | 12 | 13 | 15 | 17 |
| | 1103 | 17 | 17 | 10 | 13 | 13 | 11 | 11 | 12 | 11 | 12 |
| Group 2 | 2101 | 19 | 12 | 10 | 11 | 12 | 13 | 14 | 13 | 13 | 13 |
| | 2102 | 21 | 17 | 11 | 11 | 14 | 16 | 12 | 12 | 15 | 14 |
| | 2103 | 22 | 20 | 12 | 14 | 13 | 11 | 12 | 11 | 15 | 14 |
| Group 3 | 3101 | 19 | 21 | 11 | 10 | 13 | 16 | 13 | 12 | 15 | 15 |
| | 3102 | 21 | 19 | 10 | 13 | 12 | 14 | 11 | 11 | 17 | 17 |
| | 3003 | 18 | 17 | 10 | 10 | 11 | 10 | 12 | 13 | 13 | 16 |
| Group 4 | 4101 | 21 | 18 | 11 | 11 | 12 | 10 | 11 | 10 | 14 | 12 |
| | 4102 | 21 | 18 | 12 | 14 | 12 | 17 | 12 | 15 | 13 | 13 |
| | 4004 | 21 | 19 | 12 | 9 | 14 | 11 | 14 | 12 | 17 | 14 |
| Mean | | 19 | | 11 | | 13 | | 12 | | 15 | |
| STDEV | | 3 | | 2 | | 2 | | 1 | | 2 | |

R = Right Eye
L = Left Eye
STDEV = Standard Deviaiton

Travoprost is a mitotic agent in beagles demonstrating strong pupil constriction after administration of inventive implant. Pupil diameter measurements taken pre- and post-administration of inventive implant over the study duration are presented in Table 5. Results demonstrate sustained pupil constriction following inventive implant administration demonstrating a secondary pharmacodynamic response in beagles over the 4-month study duration.

TABLE 5

Pre- and Post- Inventive Implant Administration Pupil Diameter Measurements over the Study Duration.

| | | Month Number Relative to Start Date | | | | | | | | | |
|---|---|---|---|---|---|---|---|---|---|---|---|
| Group | Animal | Pre-Dose | | Month 1 | | Month 2 | | Month 3 | | Month 4 | |
| # | # | R | L | R | L | R | L | R | L | R | L |
| Group 1 | 1101 | 8 | 8 | 1 | 1 | 1 | 1 | 1 | 1 | 5 | 2 |
| | 1102 | 7 | 7 | 3 | 2 | <1 | 1 | 1 | 1 | 2 | 2 |
| | 1103 | 8 | 8 | 3 | 2 | 6 | 5 | 4 | 5 | 4 | 3 |
| Group 2 | 2101 | 7 | 7 | 1 | 1 | <1 | 1 | 1 | 1 | 1 | 1 |
| | 2102 | 9 | 9 | 2 | 2 | 3 | 4 | 2 | 3 | 4 | 4 |
| | 2103 | 9 | 8 | 1 | 1 | 3 | 2 | 2 | 2 | 2 | 2 |
| Group 3 | 3101 | 7 | 8 | 3 | 2 | 3 | 4 | 3 | 3 | 2 | 2 |
| | 3102 | 8 | 7 | 5 | 3 | 5 | 3 | 4 | 3 | 1.5 | 1.5 |
| | 3003 | 9 | 9 | 4 | 3 | 3 | 3 | 5 | 3 | 1 | 1 |
| Group 4 | 4101 | 8 | 8 | 3 | 3 | 3 | 3 | 3 | 3 | 1 | 1.5 |
| | 4102 | 9 | 8 | 4 | <1 | 3 | 2 | 3 | 2 | 1 | 2 |
| | 4004 | 8 | 8 | 3 | 2 | 4 | 2 | 3 | 3 | 4 | 2 |
| Mean | | 8 | | 2 | | 3 | | 3 | | 2 | |
| STDEV | | 1 | | 1 | | 1 | | 1 | | 1 | |

R = Right Eye
L = Left Eye
STDEV = Standard Deviation e. Reduction and Effects on Pupil Diameter in Dogs with Inventive (Travoprost) Implant—Hydrogel Persistence/PD/Tolerability Study The purpose of this study was to investigate pharmacodynamics (intraocular pressure "IOP" and pupil diameter "PD"), implant persistence, and eye tolerability after a single anterior chamber (intracameral) injection of inventive (travoprost) implant in male beagle dogs over a 7-month period formulated with two different persisting hydrogel formulations. Inventive implant containing 15 μg travoprost per implant formulated with either a two month persisting hydrogel (Group 1, 8-arm 15K succinimidyl glutarate) or a four month persisting hydrogel (Group 2, 8-arm 15K succinimidyl azelate) was administered via intracameral injection in 12 normotensive beagles (n=6 beagles/12 eyes per group). The Group 2 hydrogel formulation composition was the same as tested in Cohorts A (15 μg travoprost dose) and B (26 μg travoprost dose) in the Phase 1 clinical study. A solid polylactide implant (no travoprost) was administered via intracameral injection in 3 normotensive beagles (n=6 eyes) and served as a control arm in the study (Group 3). This section will discuss the IOP (primary) and pupil diameter (secondary) pharmacodynamic responses.

Intraocular pressure (IOP) was measured using a TonoVet® tonometer and pupil diameter was measured using an embossed pictorial scale on a penlight with both measurements done pre- and monthly post-dose administration. IOP results for each study group are reported in Table 6 and graphically represented as mean IOP change relative to baseline in FIG. 11. Pupil diameter results for each study group are reported in Table 7.

TABLE 6

Pre- and Post-Dose OTX-TIC Administration IOP Measurements for Each Test Group over the Study Duration.

| | Group | | | | | |
|---|---|---|---|---|---|---|
| | 1 OTX-TIC Two-month Persisting Hydrogel | | 2 OTX-TIC Four-month Persisting Hydrogel | | 3 Control | |
| Time | Mean (mmHg) | SD (mmHg) | Mean (mmHg) | SD (mmHg) | Mean (mmHg) | SD (mmHg) |
| Pre-Dose | | | | | | |
| Baseline 1 | 23.2 | 2.9 | 23.8 | 3.9 | 21.4 | 2.3 |
| Baseline 2 | 22.9 | 3.3 | 24.1 | 3.6 | 21.6 | 2.5 |
| Baseline 3 | 23.8 | 2.5 | 24.8 | 4.2 | 20.3 | 1.7 |
| Mean Baseline | 23.3 | 2.9 | 24.2 | 3.9 | 21.1 | 2.3 |
| Post-Dose | | | | | | |
| 0.5 Months | 16.6 | 2.0 | 16.0 | 2.8 | 19.7 | 2.9 |
| 1 Month | 15.1 | 1.5 | 16.7 | 4.0 | 16.0 | 1.8 |
| 1.5 Months | 19.9 | 4.9 | 21.0 | 3.2 | 21.3 | 2.1 |
| 2 Months | 15.4 | 2.5 | 18.2 | 2.8 | 18.2 | 1.7 |
| 3 Months | 17.6 | 2.1 | 20.2 | 4.3 | 19.0 | 1.5 |
| 4 Months | 18.6 | 2.2 | 19.7 | 3.6 | 19.1 | 1.9 |
| 5 Months | 20.6 | 3.3 | 23.4 | 4.4 | 19.4 | 2.8 |
| 6 Months | 21.4 | 2.7 | 24.2 | 4.1 | 20.5 | 2.5 |
| 7 Months | 22.0 | 2.8 | 26.1 | 4.6 | 22.5 | 1.3 |

SD denotes standard deviation

TABLE 7

Pre- and Post-Dose OTX-TIC Administration Pupil Diameter Measurements for Each Test Group over the Study Duration.

| | Group | | | | | |
|---|---|---|---|---|---|---|
| | 1 OTX-TIC Two-month Persisting Hydrogel | | 2 OTX-TIC Four-month Persisting Hydrogel | | 3 Control | |
| Time | Mean (mmHg) | SD (mmHg) | Mean (mmHg) | SD (mmHg) | Mean (mmHg) | SD (mmHg) |
| Baseline (pre-dose) | 7.3 | 0.5 | 7.0 | 0.6 | 6.0 | 0.0 |

TABLE 7-continued

Pre- and Post-Dose OTX-TIC Administration Pupil Diameter Measurements for Each Test Group over the Study Duration.

| | Group | | | | | |
|---|---|---|---|---|---|---|
| | 1 OTX-TIC Two-month Persisting Hydrogel | | 2 OTX-TIC Four-month Persisting Hydrogel | | 3 Control | |
| Time | Mean (mmHg) | SD (mmHg) | Mean (mmHg) | SD (mmHg) | Mean (mmHg) | SD (mmHg) |
| 0.5 Months | 1.7 | 0.7 | 1.2 | 0.4 | 6.0 | 0.9 |
| 1 Month | 2.4 | 0.7 | 2.3 | 0.8 | 7.0 | 0.0 |
| 1.5 Months | 2.7 | 0.7 | 2.7 | 0.8 | 7.7 | 1.8 |
| 2 Months | 2.8 | 0.7 | 1.5 | 0.7 | 6.7 | 0.5 |
| 3 Months | 2.4 | 1.0 | 2.0 | 0.9 | 6.7 | 0.5 |
| 4 Months | 3.3 | 1.7 | 2.5 | 1.4 | 6.3 | 0.5 |
| 5 Months | 4.6 | 1.3 | 3.0 | 1.5 | 6.3 | 1.0 |
| 6 Months | 5.5 | 0.5 | 5.2 | 1.0 | 6.7 | 0.8 |
| 7 Months | 5.5 | 0.5 | 5.3 | 0.8 | 6.3 | 0.5 |

SD denotes standard deviation

In this study, the median visual persistence of the Group 1 implant was 2 months and the Group 2 implant was 4 months. The Group 2 duration is consistent with a median persistence finding of 4 months in a previous beagle study.

Figure 11:
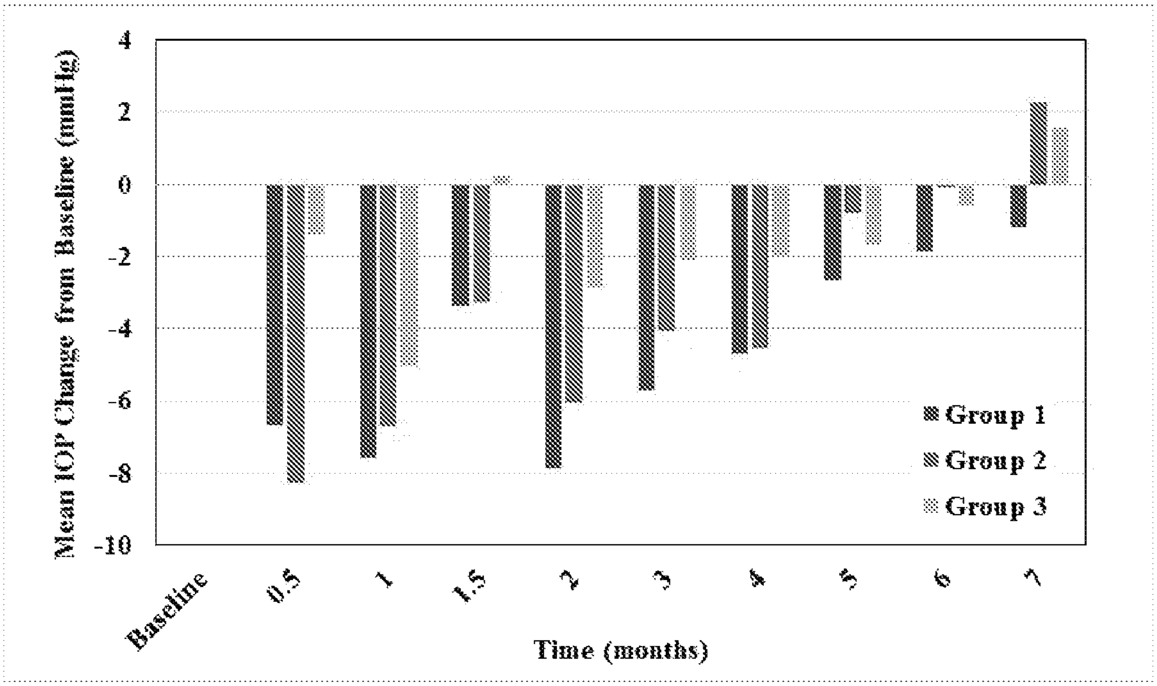
FIG. 11 shows pre- and post-dose inventive implant administration IOP change relative to baseline for each test group over the study duration.

IOP results demonstrate that the 2-month persisting hydrogel implant (Group 1) created a similar decrease in IOP compared to the 4-month persisting hydrogel implant (Group 2) through 4 months, and statistically the mean difference from baseline IOP results were within one-standard deviation between the two formulations, see Table 6 and FIG. 11. Importantly, the IOP decrease at 3 months between the present hydrogel (Group 2) or absent hydrogel (Group 1) made no difference on the TOP reduction from baseline, whereby the Group 1 hydrogel had been absent for 1 month in most eyes indicating that travoprost release from the microparticles was still regulating IOP reduction in the anterior chamber of the beagle eye. Both travoprost containing hydrogel formulations demonstrated a greater decrease in IOP compared to the control article (Group 3).

The pupil diameter (PD) measurements taken pre- and post-administration of inventive implant over the study duration for each group are presented in Table 7. Following administration through four months both inventive implant formulations (Groups 1 & 2) demonstrated a pronounced reduction in pupil diameter (≥ 4.0 mm) relative to baseline and Group 3 demonstrated no reduction in pupil diameter compared to baseline. By 6 and 7 months the pupil diameter returned to near baseline values for Groups 1 and 2.

Figure 12:
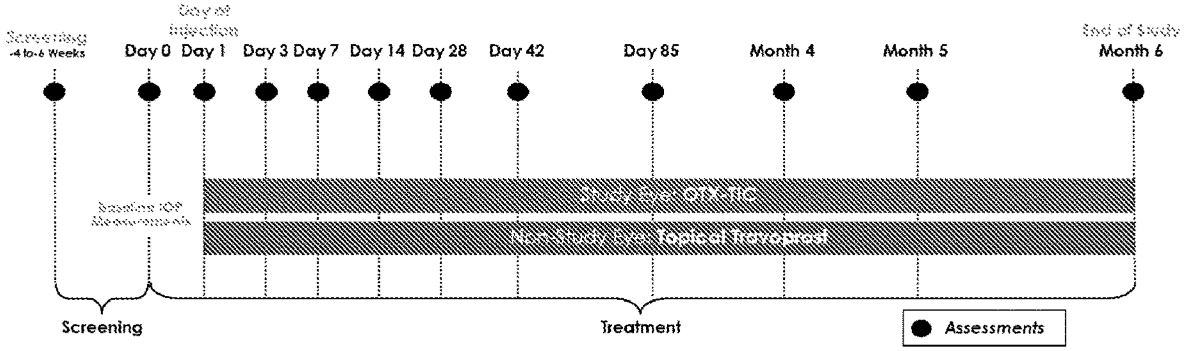
FIG. 12 shows the study design for primary open angle glaucoma or ocular hypertension trials using inventive implant.

Example 5: Safety, Tolerability and Efficacy of Inventive (Travoprost) Implant in Subjects with Primary Open-Angle Glaucoma or Ocular Hypertension A 4-month low dose (15 μg) or high dose (26 μg) of travoprost encapsulated in microparticles (4A/7A/9A/5.5E) was formulated in a 12% inventive hydrogel comprising a polymer matrix formed from 8a15K PEG-SAZ and trilysine with the 12% being the PEG weight dived by the fluid weight times 100 and was injected via 27G needle into the anterior chamber of 10 subjects over 7 months; one eye per patient treated. See FIG. 12. Patient population was controlled ocular hypertension or primary open-angle glaucoma; open, normal anterior chamber angles on gonioscopy.

Primary outcomes were as follows. Diurnal IOP (8 AM, 10 AM, 4 PM) at Baseline. Day 14. Day 42. Day 85, Month 4 and Month 6. Intraocular pressure at 8 AM at Day 1. Day 3. Day 7 and Day 28. Safety evaluations, including adverse event reporting, ocular comfort, global tolerance, BCVA, endothelial cell counts, and pachymetry.

Figure 13A:
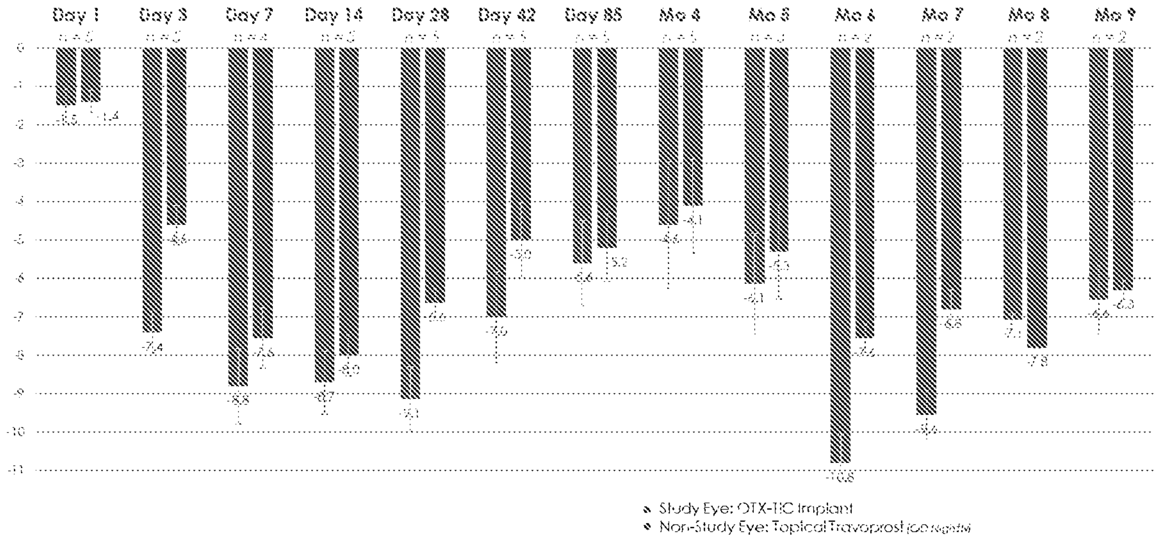
FIG. 13A shows the mean IOP Change from Baseline, Cohort 1 from the study design for primary open angle glaucoma or ocular hypertension with measurements taken at 8 AM.
Figure 13B:
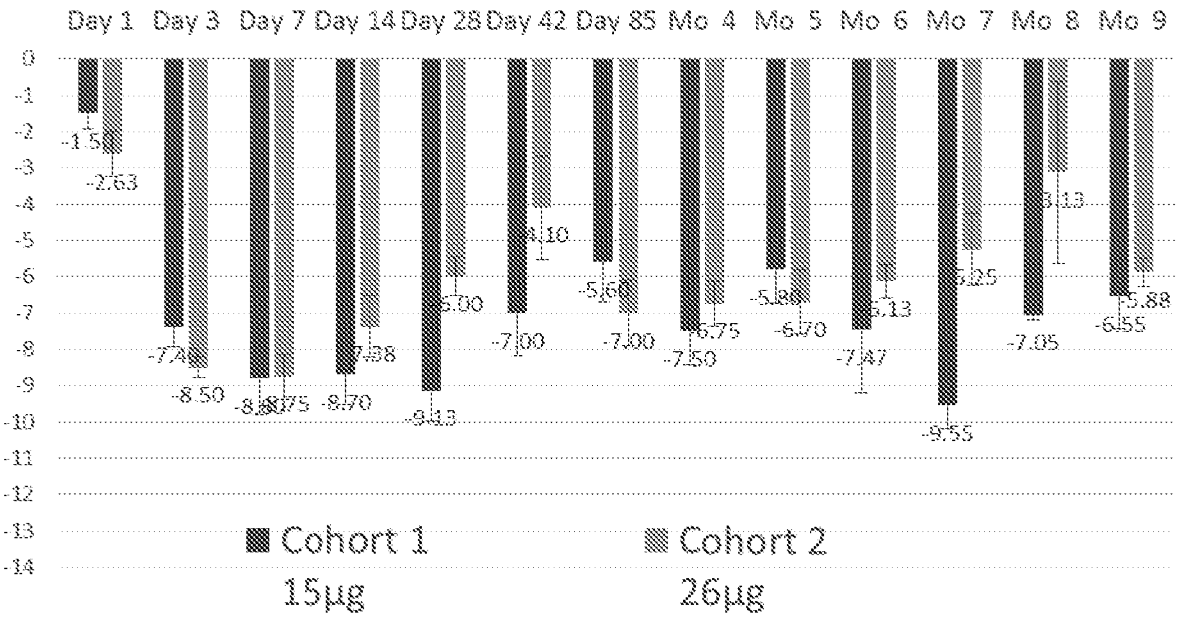
FIG. 13B compares the mean IOP Change from Baseline of different loading concentrations of travoprost from the study design for primary open angle glaucoma or ocular hypertension.

Mean IOP values were decreased in patients receiving both OTX-TIC and topical travoprost as early as two days following administration (FIGS. 13A and 13B). In patients receiving OTX-TIC, mean IOP was decreased approximately 5-11 mmHg from Day 3 through Month 9. Mean IOP values remained decreased from baseline values through the study period (Month 7) and beyond (Month 9) in two of two patients.

Figure 14:
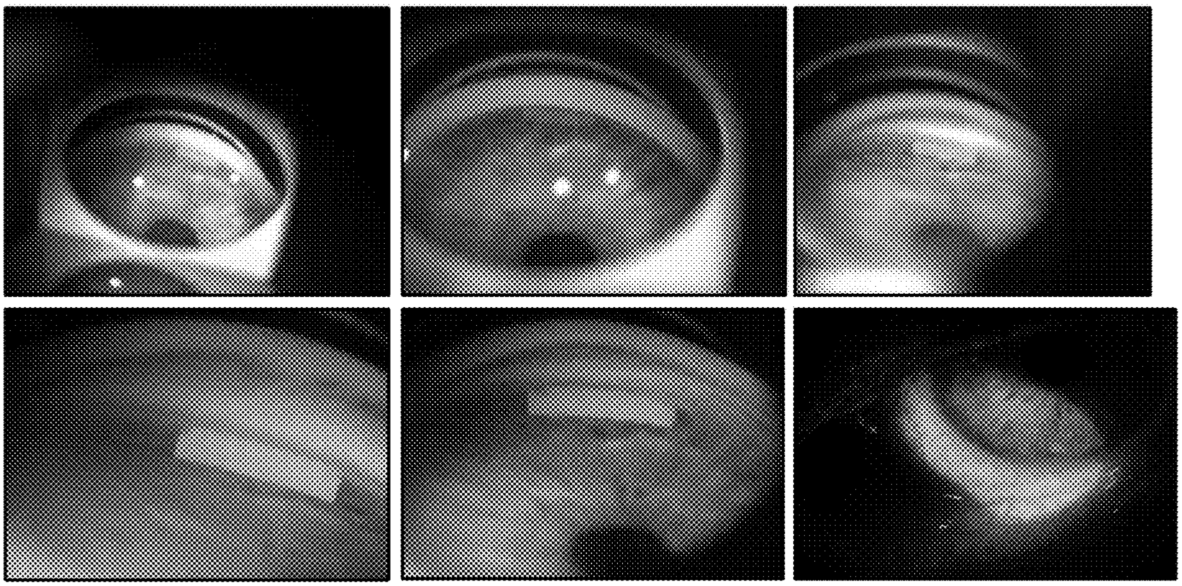
FIG. 14 shows implant resorption over a clinical study in human eyes (top, left to right) Days 1, 14, 28, and (bottom) Month 4, 5, 6.

Upon injection, implant hydrated quickly and resided in the iridocorneal angle. The implant was visualized in all subjects at all visits through 7 months (FIG. 14). The implant was not observed to move at slit lamp; in one subject, there was slight rotation noted at the Day 14 visit as compared to the Day 7 visit. Implant biodegraded in 2 of 2 subjects by Month 7.

Figure 15:
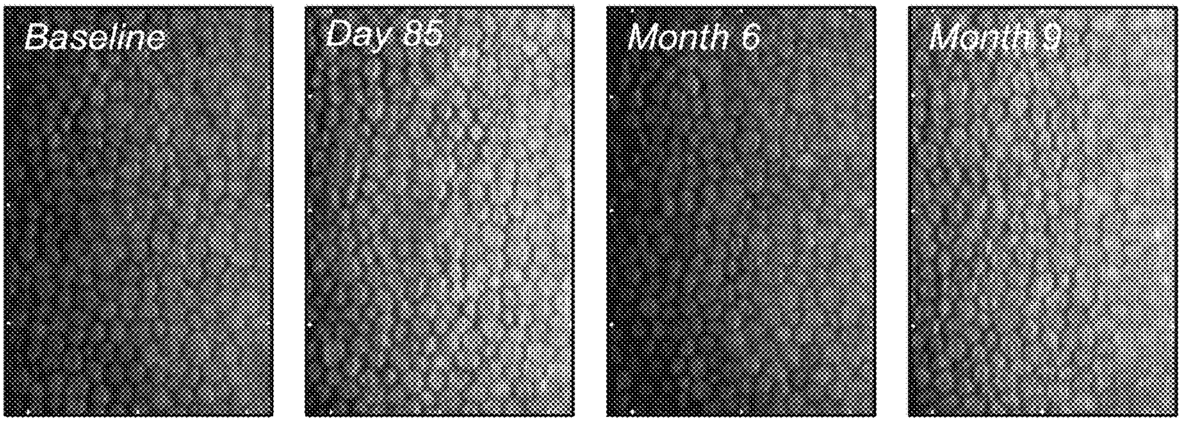
FIG. 15 illustrates the endothelial cell count over time for subjects administered inventive implant.

Safety results: Adverse events reported included iritis (n=2) and peripheral anterior synechia (n=3); all were graded by the investigator as mild or moderate. Patients received topical rescue therapy at the discretion of the investigator as IOP returned to baseline levels. 1 patient was rescued at Month 3.5. Topical brimonidine/timolol given; both eyes required treatment. No changes in endothelial cell counts or pachymetry from baseline for 5/5 subjects through Month 3; 3/3 subjects through Month 6; 2/2 subjects through Month 9 (FIG. 15). Additional studies were performed using 15 μg and 5 μg travoprost encapsulated in microparticles (4A/7A/9A and 4A/7A, respectively) in 12% for 15 μg and 15% for 5 μg hydrogels comprising a polymer matrix formed from 8a15K PEG-SG and trilysine.

While we have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The invention claimed is:

1. A sustained release biodegradable intracameral hydrogel implant comprising travoprost and a polymer network, wherein the polymer network comprises a plurality of multi-arm polyethylene glycol (PEG) units, and wherein the polymer network is formed by reacting a plurality of polyethylene glycol (PEG) units selected from PEG with a succinimidylazelate end group (SAZ), PEG with a succinimidylglutarate end group (SG) and PEG with a succinimidylsuccinate end group (SS), with one or more PEG amine groups or lysine-based amine groups.

2. A method of treating ocular hypertension in a subject in need thereof comprising administering the hydrogel implant of claim 1 to the eye of a subject.

3. A method of treating glaucoma in a subject in need thereof comprising administering the hydrogel implant of claim 1 to the eye of a subject.

4. The method of claim 3, wherein the glaucoma is open angle glaucoma.

5. The method of claim 4, wherein essentially no endothelial damage occurs following administration of a disclosed implant.

6. The hydrogel implant of claim 1, wherein the polymer network is amorphous.

7. The hydrogel implant of claim 1, wherein the polymer network is semi-crystalline.

8. The hydrogel implant of claim 1, wherein the hydrogel provides travoprost delivery to the eye in a sustained manner for a period ranging from about 2 to about 8 months.

9. The hydrogel implant of claim 1, wherein the hydrogel provides travoprost delivery to the eye to the eye in a sustained manner for a period ranging from about 3 to about 7 months.

10. The hydrogel implant of claim 1, wherein the hydrogel provides travoprost delivery to the eye in a sustained manner for a period ranging from about 4 to about 6 months.

11. The hydrogel implant of claim 1, wherein the travoprost is microencapsulated with polylactic glycolic acid.

12. The hydrogel implant of claim 1, wherein the polymer networks is conjugated to fluorescein.

13. The hydrogel implant of claim 1, wherein the implant is designed for implantation near the corneal endothelial cells.

14. The hydrogel implant of claim 1, wherein the implant is designed for implantation in the inferior iridocorneal angle.

15. The hydrogel implant of claim 1, wherein the hydrogel implant is adapted to maintain a travoprost acid concentration of at least about 10 ng/ml in aqueous humor of an eye of a subject for at least about three months after implantation into the eye of the subject.

* * * * *